(12) United States Patent
Rivet-Sabourin et al.

(10) Patent No.: US 11,426,184 B2
(45) Date of Patent: Aug. 30, 2022

(54) METHOD AND SURGICAL KIT FOR MILLING A BONE

(71) Applicant: LABORATOIRES BODYCAD INC., Québec (CA)

(72) Inventors: Geoffroy Rivet-Sabourin, Stoneham (CA); Audrey Lainé, Saint-Nicolas (CA); Stefan W. Kreuzer, Houston, TX (US); Alexandre Labrecque, Québec (CA)

(73) Assignee: LABORATOIRES BODYCAD INC., Québec (CA)

( * ) Notice: Subject to any disclaimer, the term of this patent is extended or adjusted under 35 U.S.C. 154(b) by 117 days.

(21) Appl. No.: 17/072,120

(22) Filed: Oct. 16, 2020

(65) Prior Publication Data

US 2021/0113221 A1 Apr. 22, 2021

Related U.S. Application Data

(60) Provisional application No. 62/916,327, filed on Oct. 17, 2019.

(51) Int. Cl.
*A61B 17/00* (2006.01)
*A61B 17/17* (2006.01)
*A61B 17/16* (2006.01)

(52) U.S. Cl.
CPC .. *A61B 17/1764* (2013.01); *A61B 2017/1602* (2013.01)

(58) Field of Classification Search
CPC combination set(s) only.
See application file for complete search history.

(56) References Cited

U.S. PATENT DOCUMENTS

2001/0001121 A1* 5/2001 Lombardo ......... A61B 17/1668
606/89
2018/0228614 A1 8/2018 Lang et al.

* cited by examiner

*Primary Examiner* — Sameh R Boles
(74) *Attorney, Agent, or Firm* — Marshall, Gerstein & Borun LLP

(57) ABSTRACT

A surgical kit and method for milling a bone, the surgical kit including: a rotatable milling tool including a receiving bore with an abutment portion; a positioning pin insertable in the bone for guiding the milling tool along a milling axis and towards the bone, the positioning pin including a pin shaft receivable in the receiving bore and a pin depth determination element, the pin shaft being abuttable against the abutment portion of the milling tool; and a bone milling guide positionable at a predetermined location on the bone for guiding the positioning pin when the positioning pin is inserted into the bone, the bone milling guide including a pin shaft guiding channel for receiving the pin shaft and a guide depth determination element cooperable with the pin depth determination element to provide an indication that the positioning pin is inserted in the bone at a predetermined depth.

17 Claims, 22 Drawing Sheets

METHOD AND SURGICAL KIT FOR MILLING A BONE

CROSS-REFERENCE TO RELATED APPLICATIONS

The present application claims the benefit of U.S. Provisional Patent Application No. 62/916,327, filed on Oct. 17, 2019, the specification of which is incorporated herein by reference.

TECHNICAL FIELD

The technical field generally relates to methods and tools for performing surgery, and more precisely to methods and tools for milling a bone.

BACKGROUND

In some surgical procedures, it may be necessary to mill a bone of a patient—a procedure sometimes referred to as "reaming" the bone—to create a recess on the bone which is sized and shaped to receive an implant.

For example, when performing a unicompartmental (i.e. partial) knee arthroplasty or a total knee arthroplasty, the medial condyle and/or the lateral condyle of the patient's femur may need to be milled in order to create a recess or spacing on the bone which is sized and shaped to receive or at least accommodate a femoral component of a knee implant. In other words, the bone is milled such that a portion of the bone is removed and a substantially flat surface is created. The femoral component generally sits on the flat surface and takes the place of the removed portion of the bone.

The milling of the bone is typically performed using a rotating milling tool, or reamer, powered by a motor. To ensure that the recess created by the milling has a desired size and shape to receive the implant, the milling tool may be guided using a guiding member, such as a guiding pin inserted in the bone prior to the milling. Unfortunately, existing guiding pins and existing methods of inserting the guiding pin in the bone may be complex, imprecise and/or may rely heavily on the skills of a surgeon performing the surgery to make sure that the guiding pin is positioned and oriented so as to properly guide the milling tool.

SUMMARY

According to one aspect, there is provided a surgical kit for milling a bone, the surgical kit comprising: a milling tool rotatable about a milling axis, the milling tool including a milling face for contacting the bone, a central pin receiving bore extending along the milling axis and an abutment portion extending into the central pin receiving bore; a positioning pin insertable in the bone and engageable by the milling tool for guiding the milling tool along the milling axis and towards the bone, the positioning pin including a pin shaft receivable in the central pin receiving bore of the milling tool and a pin depth determination element located at a predetermined position on the pin shaft, the pin shaft being abuttable against the abutment portion of the milling tool to prevent further movement of the milling tool towards the bone along the milling axis; and a bone milling guide positionable at a predetermined location on the bone and engageable by the positioning pin when the positioning pin is inserted into the bone, the bone milling guide including a pin shaft guiding channel sized and shaped to receive the pin shaft therein, the bone milling guide further including a guide depth determination element located adjacent the pin shaft guiding channel, the guide depth determination element being configured to cooperate with the pin depth determination element to provide an indication that the positioning pin is inserted in the bone at a predetermined depth.

In at least one embodiment, the pin depth determination element comprises a stopper mounted to the pin shaft and wherein the guide depth determination element comprises an abutment portion, the abutment portion being abuttable against the stopper when the positioning pin is inserted into the bone through the pin shaft guiding channel to prevent further insertion of the positioning pin into the bone.

In at least one embodiment, the stopper is removably mounted to the pin shaft.

In at least one embodiment, the stopper extends radially outwardly from the pin shaft.

In at least one embodiment, the stopper is penannular and comprises an inner side face defining a central opening, an outer side face spaced radially outwardly from the inner side face and an access notch extending from the outer side face to the inner side face.

In at least one embodiment, the notch tapers from the outer side face to the inner side face.

In at least one embodiment, the pin shaft comprises an annular groove, the stopper being sized and shaped to be received in the central opening of the stopper to prevent movement of the stopper along the pin shaft.

In at least one embodiment, the pin shaft comprises a proximal pin portion insertable into the bone and a distal pin portion detachably connectable to the proximal pin portion.

In at least one embodiment, the proximal pin portion comprises a proximal connector and the distal pin portion comprises a distal connector engageable with the proximal connector to connect the proximal pin portion to the distal pin portion.

In at least one embodiment, the proximal and distal connectors are configured such that rotation of the distal shaft portion in a first rotation direction rotates the proximal shaft portion in the first rotation along with the distal shaft portion, and rotation of the distal shaft portion in a second rotation direction opposite the first rotation direction detaches the distal shaft portion from the proximal shaft portion.

In at least one embodiment, the distal pin portion is hollow to allow an elongated screwing tool to extend longitudinally through the distal pin portion to engage the distal end of the proximal pin portion such that rotation of the elongated tool in the first rotation direction rotates the positioning pin.

In at least one embodiment, the bone milling guide including a guide body having a bone-contacting face configured to be placed against the bone and a pin-engaging face opposite the bone-contacting face, the bone-contacting face being sized and shaped to substantially conform to surface contours of the bone at the predetermined location on the bone.

In at least one embodiment, the pin shaft guiding channel comprises a positioning pin receiver extending away from the pin-engaging face of the guide body, the positioning pin receiver having a bone-insertion end secured to the guide body and a distal end located away from the body, the distal end comprising the abutment portion of the bone milling guide.

In at least one embodiment, the milling tool comprises an operative portion engageable with the bone to mill the bone and a shank portion operatively couplable with a rotary actuator for rotating the milling tool.

In at least one embodiment, the operative portion of the milling tool comprises a milling face for contacting the bone, the milling face extending in a milling plane oriented generally orthogonally to the milling axis.

In at least one embodiment, the central pin receiving bore extends along the milling axis between the milling face and an inner end face located away from the milling face and towards the shank portion, the inner end face defining the abutment portion of the milling tool.

In at least one embodiment, the operative portion further comprises a pair of side openings located radially opposite each other and adjacent the inner end face.

According to another aspect, there is also provided a positioning pin in combination with a bone milling guide, the bone milling guide comprising: a guide body having a bone-contacting face superposable against the bone and a guide depth determination element; and the positioning pin comprising: a pin shaft insertable in a bone and defining a milling axis when inserted therein, the pin shaft being engageable with a milling tool and abuttable against an abutment portion of the milling tool to prevent further movement of the milling tool towards the bone along the milling axis; and a pin depth determination element located on the pin shaft, the pin depth determination element being configured to cooperate with the guide depth determination element of the bone milling guide to provide an indication that the positioning pin is inserted in the bone at a predetermined depth.

In at least one embodiment, the pin depth determination element comprises a stopper mounted to the pin shaft, the stopper being abuttable with an abutment portion of the bone milling guide.

In at least one embodiment, the stopper is removable from the pin shaft to allow the milling tool to engage the pin shaft to mill the bone once the positioning pin has been inserted into the bone.

According to yet another aspect, there is also provided a method for milling a bone, the method comprising: positioning the bone milling guide as claimed in claim 18 on a bone, the bone milling guide including a pin shaft guiding channel extending therethrough and oriented towards the bone; inserting the positioning pin as claimed hereinabove through the pin shaft guiding channel and into the bone until the pin depth determination element cooperates with the guide depth determination element to provide an indication that the positioning pin extends out of the bone by a predetermined length; removing the bone milling guide from the bone; inserting the milling tool over the positioning pin such that the positioning pin is received in a central pin receiving bore of the milling tool and such that a milling surface of the milling tool contacts the bone, the central pin receiving bore extending along the milling axis of the milling tool; rotating the milling tool about the milling axis to mill the bone while moving the milling tool towards the bone until an abutment portion of the milling tool abuts the positioning pin to prevent further movement of the milling tool towards the bone.

In at least one embodiment, the pin depth determination element comprises a stopper mounted to the pin shaft of the positioning pin and wherein the guide depth determination element comprises an abutment portion of the bone milling guide adjacent the pin shaft guiding channel, and further wherein inserting the positioning pin through the pin shaft guiding channel comprises inserting the positioning pin through the pin shaft guiding channel until the stopper abuts the abutment portion of the bone milling guide.

In at least one embodiment, the method further comprises, after inserting the positioning pin assembly through the pin shaft guiding channel: removing the stopper from the positioning pin.

In at least one embodiment, the method further comprises, after positioning the bone milling guide on the bone: removably securing the bone milling guide to the bone.

In at least one embodiment, removably securing the bone milling guide to the bone comprises: fastening the bone milling guide to the bone using at least one fastener.

In at least one embodiment, removing the bone milling guide from the bone comprises: unfastening the bone milling guide from the bone.

In at least one embodiment, inserting the positioning pin into the bone comprises: screwing the positioning pin into the bone.

In at least one embodiment, the pin shaft of the positioning pin comprises a pin shaft having a proximal shaft portion insertable into the bone and a distal shaft portion removably connected to the proximal shaft portion, the method further comprising, after rotating the milling tool: removing the distal shaft portion from the proximal shaft portion.

In at least one embodiment, inserting a positioning pin comprises screwing the positioning pin into the bone by rotating the positioning pin in a first rotation direction, and wherein removing the distal shaft portion from the proximal shaft portion comprises: rotating the distal shaft portion in a second rotation direction opposite the first rotation direction.

In at least one embodiment, the method further comprises, after removing the distal shaft portion from the proximal shaft portion: attaching a second distal shaft portion to the proximal shaft portion, the second distal shaft portion being shorter than the distal shaft portion; inserting the milling tool over the second distal shaft portion; rotating the milling tool about the milling axis to further mill the bone while moving the milling tool towards the bone until the abutment portion of the milling tool abuts the second distal shaft portion to prevent further movement of the milling tool towards the bone.

According to another aspect, there is also provided a positioning pin for guiding a milling tool during milling of a bone, the positioning pin comprising: a pin shaft having a proximal shaft portion at least partially insertable in the bone and a distal shaft portion, the proximal shaft portion having a bone-insertion end and a distal insertion portion end, opposed to the bone-insertion end, the pin shaft defining a milling axis, the distal shaft portion being engageable by the milling tool for guiding the milling tool along the milling axis and towards the bone, the distal shaft portion being removably connectable to the distal insertion portion end of the proximal shaft portion and being abuttable with an abutment portion of the milling tool when the milling tool engages the distal shaft portion to thereby prevent further movement of the milling tool towards the bone along the milling axis.

DETAILED DESCRIPTION

Figure 1:
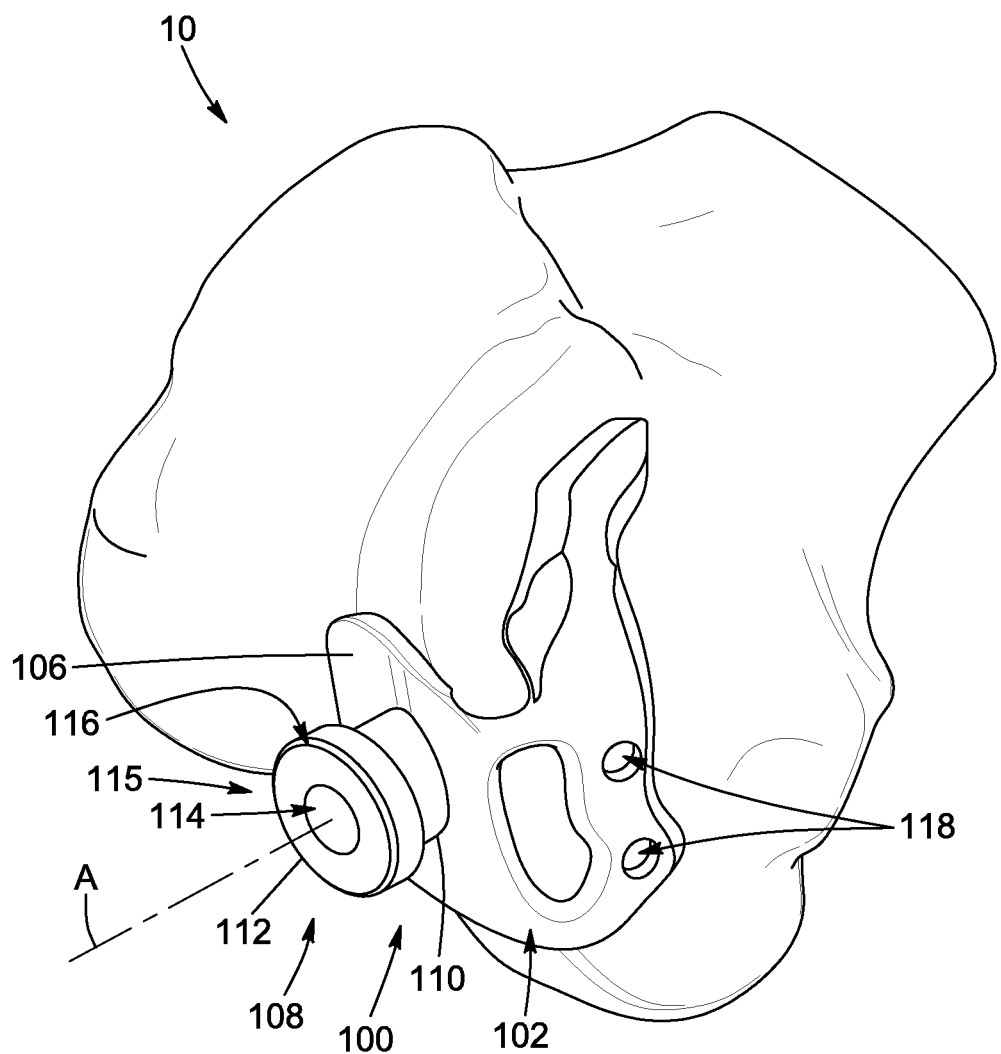
FIG. 1 is a front perspective view of a bone milling guide from a bone milling kit, in accordance with one embodiment, showing the bone milling guide placed against a patient's femoral condyle.

It will be appreciated that, for simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art, that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way but rather as merely describing the implementation of the various embodiments described herein.

For the sake of simplicity and clarity, namely so as to not unduly burden the figures with several references numbers, not all figures contain references to all the components and features, and references to some components and features may be found in only one figure, and components and features of the present disclosure which are illustrated in other figures can be easily inferred therefrom. The embodiments, geometrical configurations, materials mentioned and/or dimensions shown in the figures are optional, and are given for exemplification purposes only.

Moreover, it will be appreciated that positional descriptions such as "above", "below", "top", "bottom", "forward", "rearward" "left", "right" and the like should, unless otherwise indicated, be taken in the context of the figures and correspond to the position and orientation in the surgical kit and corresponding parts when being used. Positional descriptions should not be considered limiting.

It will further be appreciated that the term "proximal" as used hereinafter is intended to mean "close to or towards the bone" while the term "distal" is intended to mean "away from the bone".

Figure 2:
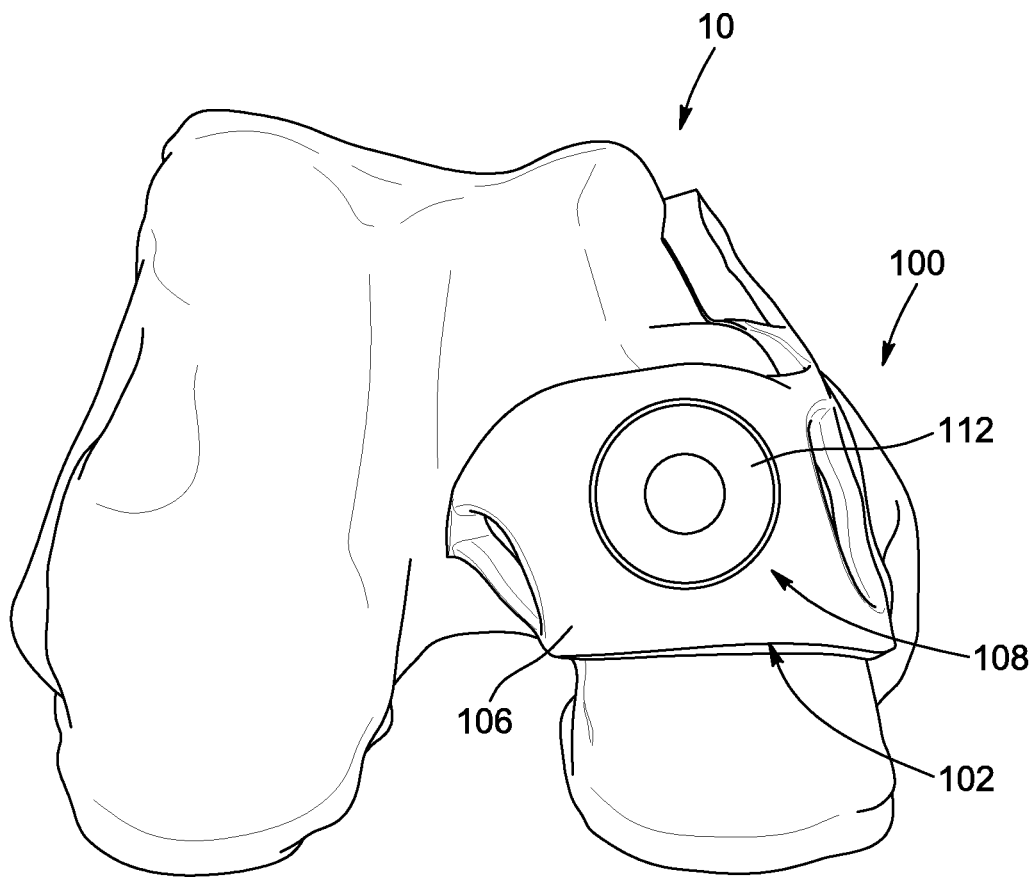
FIG. 2 is a front elevation view of the bone milling guide illustrated in FIG. 1.
Figure 3:
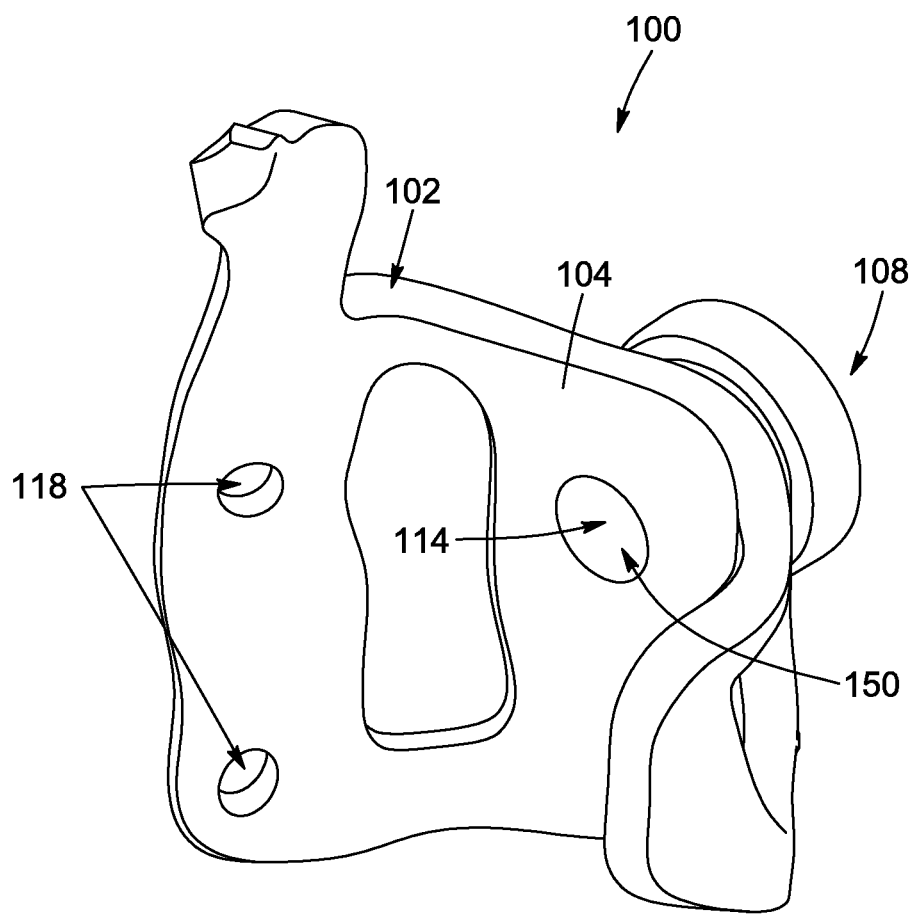
FIG. 3 is a rear perspective view of the bone milling guide illustrated in FIG. 1, with the bone milling guide shown in isolation.
Figure 5:
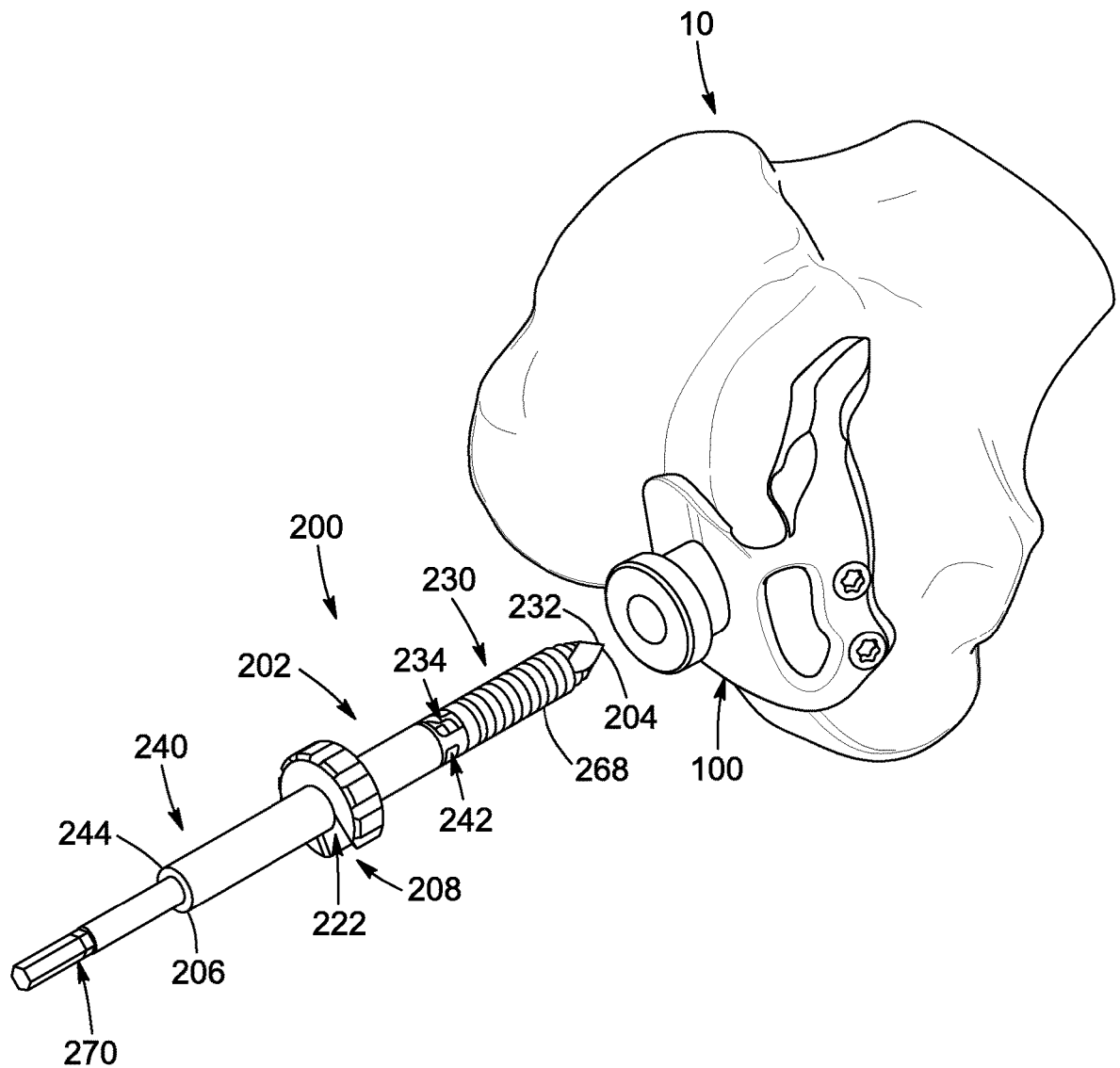
FIG. 5 is a front perspective view of the bone milling guide illustrated in FIG. 1 with a positioning pin aligned for insertion in the bone, in accordance with one embodiment.
Figure 10:
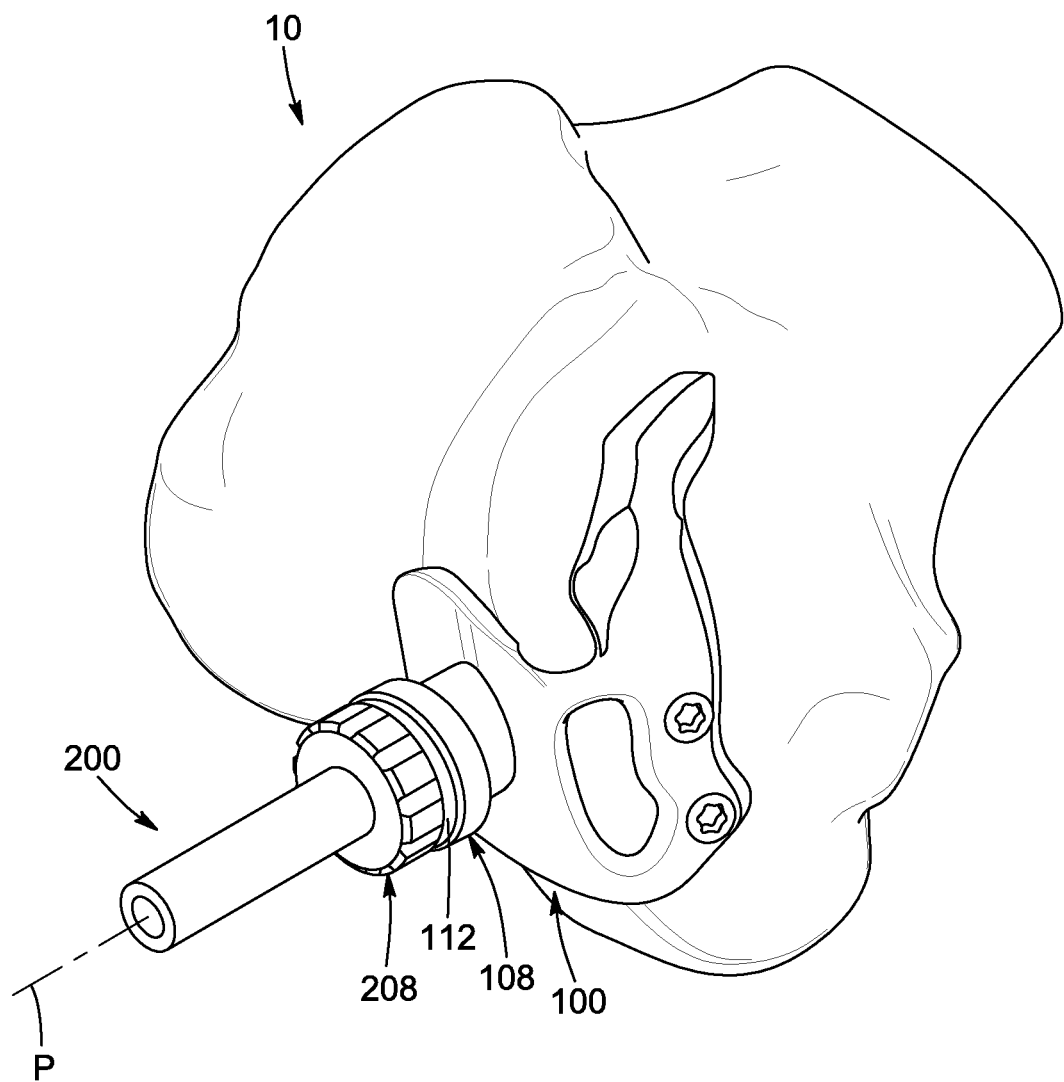
FIG. 10 is a front perspective view of the positioning pin inserted in the bone through the bone milling guide illustrated in FIG. 5.
Figure 14:
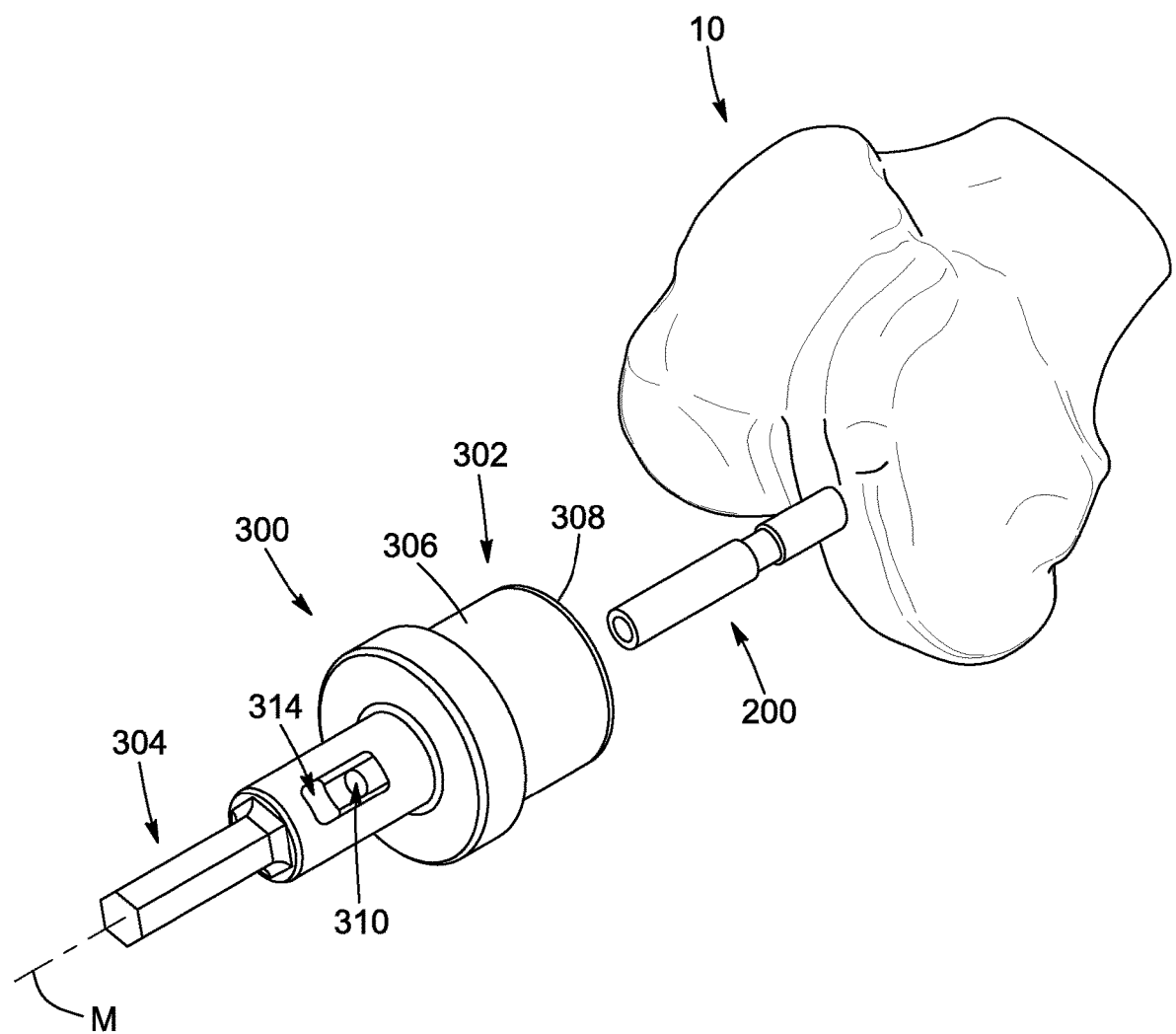
FIG. 14 is a front perspective view of the positioning pin illustrated in FIG. 5 and a milling tool aligned with the positioning pin, in accordance with one embodiment.
Figure 15:
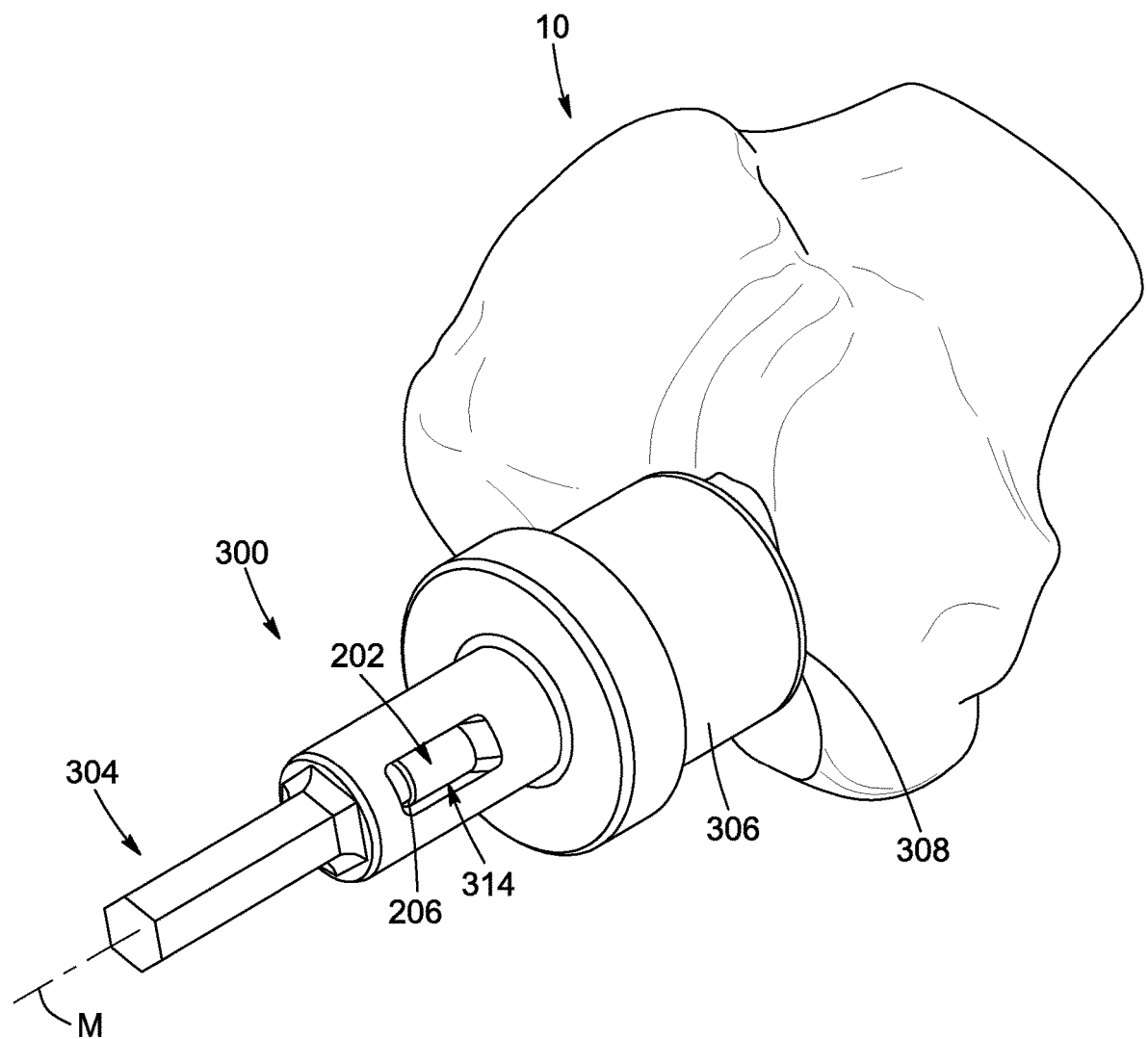
FIG. 15 is a front perspective view of the milling tool engaging the positioning pin illustrated in FIG. 14, showing the milling tool abutting the bone and configured to mill same.
Figure 16:
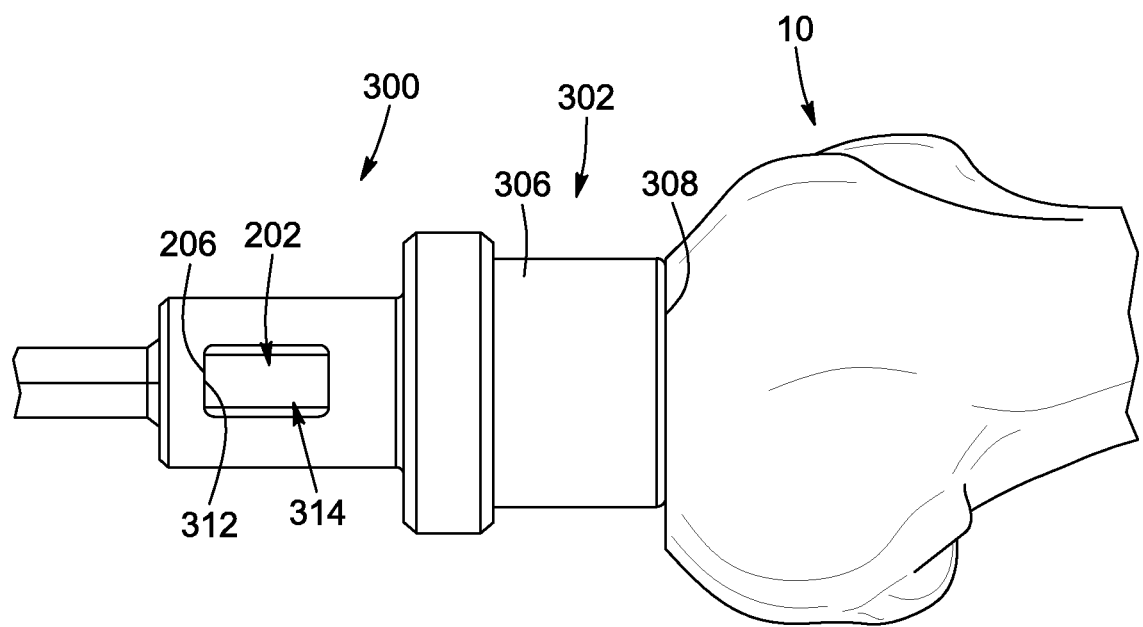
FIG. 16 is a side elevation view of the milling tool engaging the positioning pin illustrated in FIG. 14, showing the positioning pin abutting the milling tool.

Referring now to FIGS. 1 to 3, there is shown a bone milling guide 100 which forms part of a surgical kit for milling a bone 10 (or bone milling kit), in accordance with one embodiment. In the illustrated embodiment, the bone milling guide 100 is adapted for guiding the placement and orientation of a positioning pin 200, as shown in FIGS. 5 and 10, as the positioning pin 200 is being inserted into the bone 10 at a desired location on the bone 10 according to a desired orientation and up to a desired depth in the bone 10. The positioning pin 200 is adapted to guide a milling tool 300 towards the bone 10, as shown in FIGS. 14 to 16, such that the milling tool 300 may mill the bone 10 and create a recess in the bone having a desired size, depth and shape, as will be explained further below.

In the embodiment illustrated in FIG. 1, the bone milling guide 100 is placed against the bone 10, i.e. it is superposed against an outer surface of the bone 10 may include cartilage or be substantially cartilage-free. More specifically, in this embodiment, the bone 10 includes a patient's femur and, more particularly, a distal end thereof and the bone milling guide 100 is placed against a patient's femoral condyle. Alternatively, the bone to be milled could include another bone instead of the patient's femur, and the bone milling guide 100 could be placed against any appropriate portion of the bone 10 into which a recess is to be milled.

Still referring to FIGS. 1 to 3, the bone milling guide 100 includes a guide body 102 having a bone-contacting face 104 adapted to be placed against the bone 10 and a pin-engaging face 106 located opposite the bone-contacting face 104. In the embodiment shown and as will be described in further details below, the guide body 102 is patient-specific and its bone-contacting face 104 is shaped to conform to the outer surface of the bone 10 against which it is superposed. In other words, the bone-contacting face 104 of the guide body 102 matches the outer surface of the bone 10 against which it is superposed.

In the illustrated embodiment, the bone milling guide 100 further includes a positioning pin receiver 108 which extends away from the pin-engaging face 106 of the guide body 102, i.e. it protrudes outwardly from the guide body 102 from the pin-engaging face 106. The positioning pin receiver 108 includes a proximal end 110 secured to the guide body 102 and a free distal end 112 located away from the guide body 102. The bone milling guide 100 further includes a pin shaft guiding channel 114 which extends through the positioning pin receiver 108 and through the guide body 102, between the distal end of the positioning pin receiver 108 and the bone-contacting face 104 of the guide body 102. The pin shaft guiding channel 114 is opened at both ends and has a proximal end 150 with an open port provided on the bone-contacting face 104 of the guide body 102 and a distal end 152 with an open port provided at the distal end 112 of the positioning pin receiver 108.

The guiding channel 114 is sized and shaped to receive the positioning pin 200 and to guide the positioning pin 200 towards the bone 10. Specifically, the guiding channel 114 is generally linear and extends along a channel axis A, and the bone milling guide 100 is configured such that when the bone-contacting face 104 of the bone milling guide 100 is placed against the bone 10, the channel axis A extends through the bone 10. This allows the positioning pin 200 to be inserted through the guiding channel 114 along the channel axis A and into the bone 10 when the bone milling guide 100 is superposed against the bone 10.

In the illustrated embodiment, the distal end 112 of the positioning pin receiver 108 is provided with a guide depth determination element, embodied by an abutment portion 115, which cooperates with the positioning pin 200 to prevent the positioning pin 200 from being inserted into the bone past a predetermined depth, as will be further explained below.

Still in the illustrated embodiment, the positioning pin receiver 108 includes an annular projection 116, which extends radially outwardly from a remaining portion of the positioning pin receiver 108, at the distal end 112 of the positioning pin receiver 108. It will be understood that the annular projection 116 provides the abutment portion 115 defined by the distal end 112 of the positioning pin receiver 108 with a larger surface area than if the positioning pin receiver 108 did not include the annular projection 116. Alternatively, the positioning pin receiver 108 may not include an annular projection. In yet another embodiment, the bone milling guide 100 may not include the positioning pin receiver 108, and the abutment portion 115 (or the guide depth determination element) may be defined directly on the pin-engaging face 106 of the guide body 102.

In the illustrated embodiment, the bone milling guide 100 is further adapted to be secured to the bone 10 once the bone milling guide 100 has been positioned at the predetermined location on the bone 10. Specifically, the bone milling guide 100 includes a plurality of fastener openings 118 which extends through the guide body 102 and are spaced-apart from the guiding channel 114. The fasteners openings 118 are sized and shaped to receive mechanical fasteners 120, such as and without being limitative bone screws, shown in FIGS. 4, 5 and 10 to 12, for fastening the bone milling guide 100 to the bone 10. In this embodiment, the bone milling guide 100 is removably attached to the bone 10 and can be removed from the bone 10 simply by unfastening the mechanical fasteners 120. In the non-limitative embodiment shown, the mechanical fasteners 120 are bone screws. Alternatively, the mechanical fasteners 120 could be any fasteners which a skilled person would consider to be suitable.

In the illustrated embodiment and as mentioned above, the bone-contacting face 104 of the guide body 102 is patient-specific and is configured to conform to surface contours of the patient's bone 10 at a predetermined location on the bone 10. More specifically, this predetermined location on the bone 10 may be unique such that if the bone milling guide 100 is placed against the bone 10 at any other location, the bone-contacting face 104 of the guide body 102 will not fully contact the bone 10. In other words, the bone-contacting face 104 of the guide body 102 is complementary in shape to the bone surface against which it is superposed at the predetermined location. This allows a user, such as a surgeon performing a surgery using the bone milling guide 100, to place the bone milling guide 100 at the predetermined location on the bone 10 and therefore to guide the positioning pin 200 to a desired location on the bone 10 and/or at a desired angle relative to the bone 10, thereby eliminating the need for the surgeon to measure the bone 10, mark the bone 10 or use any other tool to determine the position of the desired location for the positioning pin 200 during surgery. In one embodiment, this may be accomplished by fabricating the bone milling guide 100 such that it is customized to the patient's bone, and then providing the customized bone milling guide 100 to the surgeon for performing the surgery. The patient's bone or part of the patient's bone could be scanned or otherwise modeled and the bone milling guide 100 may be designed and manufactured according to the modeled bone during surgery planning. Alternatively, the bone-contacting face 104 of the guide body 102 may not be patient-specific. Instead, during surgery, the surgeon may first determine the position of the desired location for the positioning pin 200 (e.g. by measuring the bone 10, marking the bone 10 or using any other appropriate tool) and may then place the bone-contacting face 104 of the guide body 102 against the bone 10 at the determined position such that the channel axis A of the guide body 102 intersects the bone 10 at the desired location for the positioning pin 200.

Referring now to FIGS. 5 to 9, the positioning pin 200 includes a pin shaft 202 which has a bone-insertion (or proximal) end 204 configured to be at least partially inserted into the bone 10 and a distal end 206 opposite the bone-insertion end 204. The positioning pin 200 further includes a pin depth determination element and, more particularly, a stopper 208 which is adapted to abut the abutment portion 115 of the bone milling guide 100 when the positioning pin 200 is inserted in the guiding channel 114. More specifically, in the illustrated embodiment, the stopper 208 is adapted to abut the distal end 112 of the guide's positioning pin receiver 108.

In the illustrated embodiment, the stopper 208 is removably mounted to the pin shaft 202. Specifically, once the positioning pin 200 has been inserted in the bone 10 through the bone milling guide 100 such that the stopper 208 abuts the distal end 112 of the guide's positioning pin receiver 108, the stopper 208 may be removed from the pin shaft 202 to allow the pin shaft 202 to be engaged by the milling tool 300, as will be explained further below.

Figure 9:
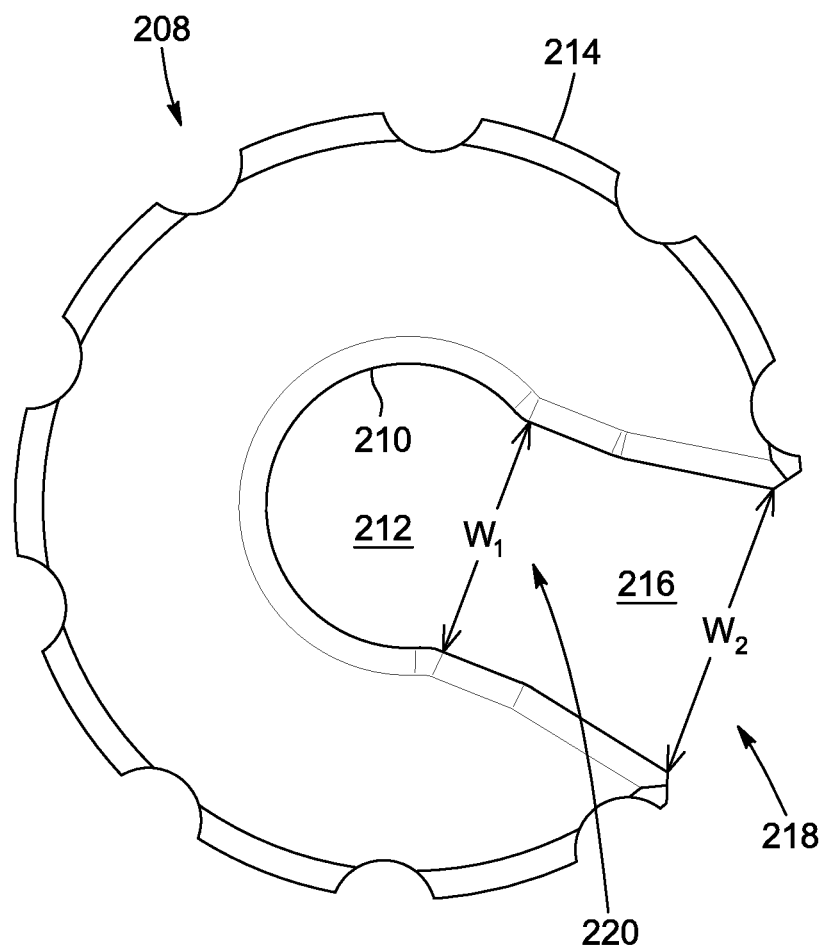
FIG. 9 is a front elevation view of a stopper for the positioning pin illustrated in FIG. 5.

As best shown in FIG. 9, the stopper 208 is substantially penannular and includes an inner side face 210 defining a central opening 212, an outer side face 214 and an access notch 216. The outer side face 214 is spaced radially outwardly from the inner side face 210 and extends substantially concentrically to the inner side face 210, and the access notch 216 extends from the outer side face 214 to the inner side face 210. Specifically, the access notch 216 includes an outer end 218 located at the outer side face 214 and an inner end 220 located at the inner side face 210. The access notch 216 allows access laterally into the central opening 212. More specifically, the access notch 216 is sized and shaped to allow the pin shaft 202 to be slid laterally in the central opening 212 through the access notch 216. Similarly, to remove the stopper 208 from the pin shaft 202, the pin shaft 202 is slid outwardly of the central opening 212 through the access notch 216.

Figure 11:
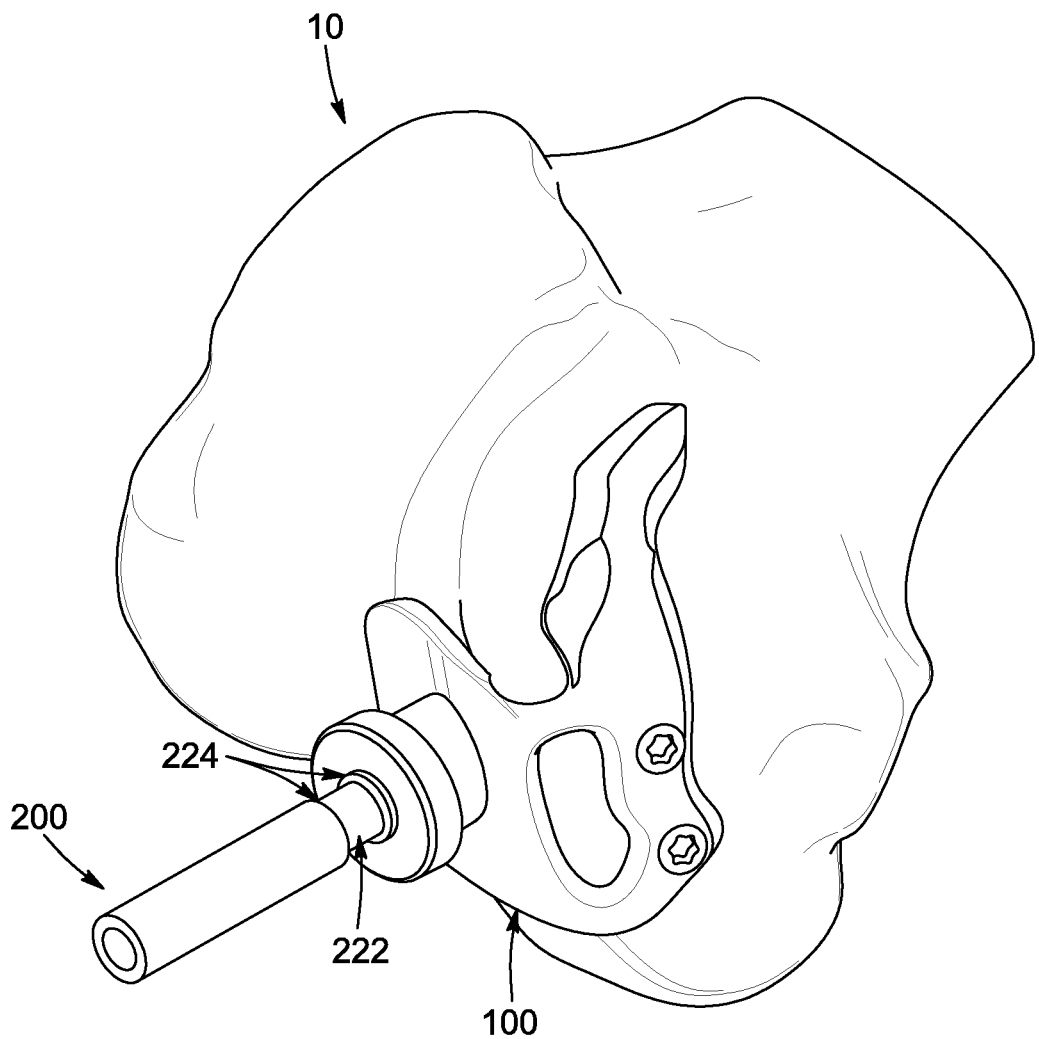
FIG. 11 is a front perspective view of the positioning pin inserted in the bone through the bone milling guide illustrated in FIG. 5, with the stopper removed from the positioning pin.
Figure 12:
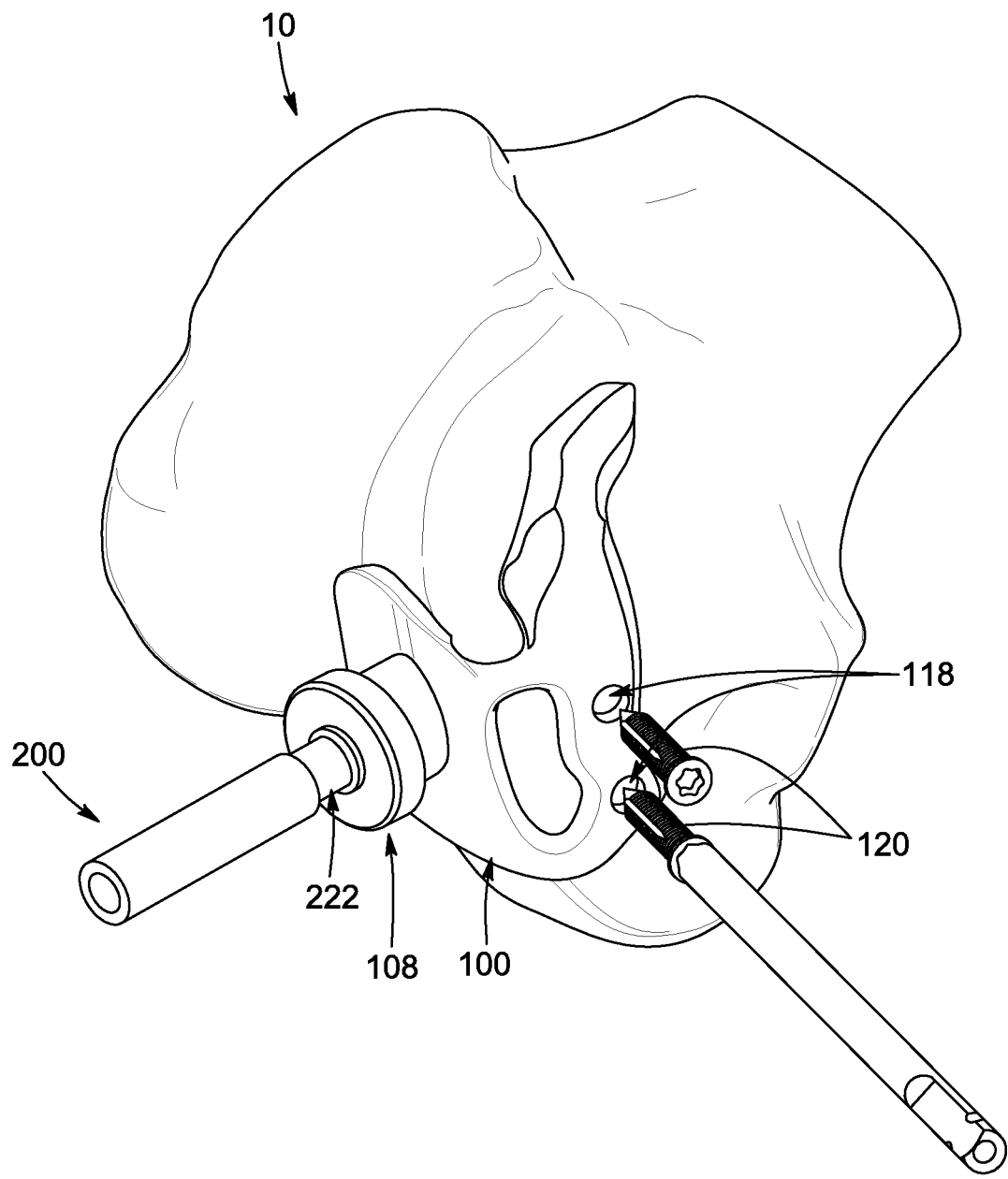
FIG. 12 is a front perspective view of the positioning pin inserted in the bone through the bone milling guide illustrated in FIG. 5, with the bone milling guide being unfastened from the bone.
Figure 13:
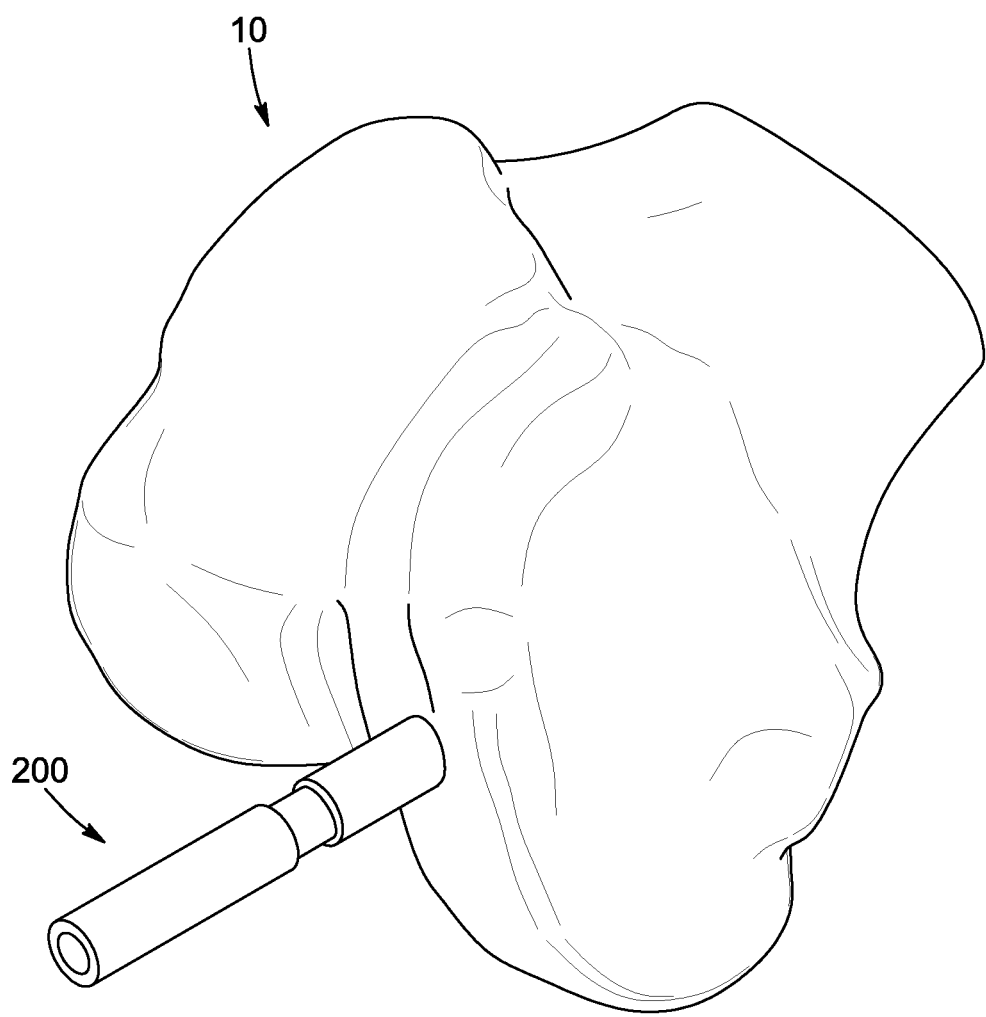
FIG. 13 is a front perspective view of the positioning pin illustrated in FIG. 5, showing the positioning pin inserted in the bone and with the guide removed.

In the illustrated embodiment, the pin shaft 202 includes an annular groove 222, best shown in FIGS. 11 to 13, which is sized and shaped to receive the stopper 208. The pin shaft 202 has a smaller diameter in the section corresponding to the annular groove 222 than in the adjacent sections, i.e. the proximal and distal sections located on a respective side of the annular groove 222. Specifically, the annular groove 222 is defined between and delimited by a pair of spaced-apart annular shoulders 224 which are spaced apart from each other by a distance which corresponds substantially to a thickness of the stopper 208. When the stopper 208 engages the annular groove 222, the stopper 208 is therefore received snuggly between the annular shoulders 224 and is therefore prevented from moving axially along the pin shaft 202.

It will be understood that the location of the annular groove 222 along the pin shaft 202 between the bone-insertion end 204 and the opposite distal end 206 thereby defines a longitudinal location of the stopper 208 along the pin shaft 202. The location of the annular groove 222 along the pin shaft 202 is therefore selected such that when the stopper 208 abuts the distal end 112 of the guide's positioning pin receiver 108, the positioning pin 200 is partially inserted into the bone 10 and extends out from the bone 10 by a desired length. When the milling tool 300 is inserted over the pin shaft 202 and is rotated to mill the bone 10, the milling tool 300 will mill the bone 10 to a desired depth which is defined by the length of the pin shaft 202 extending out of the bone 10, as will be explained further below. Alternatively, instead of an annular groove 222, the pin shaft 202 could include one or more projections or any other element that could be used to set a longitudinal position of the stopper 208 along the pin shaft 202 at a desired location.

In the illustrated embodiment, the access notch 216 substantially tapers from the outer side face 214 to the inner side face 210. Specifically, the inner end 220 of the access notch 216 has a first width $W_1$ and the outer end 218 has a second width $W_2$ which is greater than the first width $W_1$. In this configuration, the access notch 216 and the central opening 212 generally define together a keyhole shape, as shown in FIG. 9, which may facilitate the lateral insertion of the pin shaft 202 into the central opening 212 through the access notch 216. Alternatively, the access notch 216 may not taper, and the inner and outer ends 220, 218 of the access notch 216 may instead have substantially the same width.

Still in the illustrated embodiment, the central opening 212 has a diameter which generally corresponds to a diameter of the pin shaft 202 at the annular groove 222 to snuggly receive the pin shaft 202, but the width of the inner end 220 of the access notch 216 is slightly smaller than the diameter of the pin shaft 202 at the annular groove 222. Furthermore, the stopper 208 is slightly resilient such that the stopper 208 may slightly deform as the pin shaft 202 moves through the access notch 216 and into the central opening 212. This configuration allows the stopper 208 to be substantially snapped on the pin shaft 202 and to be removed from the pin shaft 202 by slightly pulling on the stopper 208 laterally to move the pin shaft 202 out of the central opening 212. Alternatively, instead of the width of the inner end 220 of the access notch 216 being smaller than the diameter of the pin shaft 202 at the annular groove 222, the stopper 208 could include a projection extending in the access notch 216 or could have any other configuration which allows the stopper 208 to be snapped on the pin shaft 202. In yet another embodiment, the stopper 208 may not be resilient and may instead be internally threaded or be configured according to any other configuration suitable for temporarily retaining the stopper 208 on the pin shaft 202 as the pin shaft 202 is inserted in the bone 10.

In the illustrated embodiment, the outer side face 214 generally has the shape of an arc of a circle and extends substantially concentrically to the inner side face 210. Alternatively, the outer side face 214 could instead be rectangular, triangular or have any other suitable shape. Moreover, in the illustrated embodiment, the outer side face 214 of the stopper 208 is textured to facilitate the manipulation of the stopper 208 but, alternatively, the outer side face 214 may not be textured and may instead be substantially smooth.

It will be appreciated that the configuration of the stopper 208 disclosed above is merely provided as an example and that the stopper 208 may have a different configuration. For example, in one embodiment, the stopper 208 may not even include an access notch, and may be removable from the pin shaft 202 by simply sliding the stopper 208 along the pin shaft 202 towards the distal end of the pin shaft 202. In yet another embodiment, the stopper 208 may not be removable from the pin shaft 202 and may instead be secured to the pin shaft 202. It will also be appreciated that other embodiments of the positioning pin can include other pin depth determination element(s) than the stopper, provided on the pin shaft at a predetermined position, to prevent further movement of the milling tool 300 towards the bone along a milling axis M (FIG. 14) and/or to cooperate with a guide depth determination element of the bone milling guide, i.e. the abutment portion 115 in the embodiment shown. In an embodiment, the abutment portion of the milling tool 300 is abuttable against the pin depth determination element to prevent further movement of the milling tool 300 towards the bone along the milling axis M. In another or the same embodiment, the guide depth determination element may be cooperable with the pin depth determination element to provide an indication that the positioning pin is inserted in the bone at a predetermined depth.

In the embodiment illustrated in FIGS. 1 to 9, the pin shaft 202 is not made from a single, continuous piece of material extending from the bone-insertion end 204 to the distal end 206, but is instead made from two distinct shaft segments or portions which are assembled together. Specifically, the pin shaft 202 includes a proximal shaft portion or insertion portion 230 located towards the bone-insertion end 204 of the positioning pin 200 and a distal shaft portion or extension portion 240 located towards the distal end 206. The insertion portion 230 includes a proximal insertion portion end 232 which coincides or corresponds with the bone-insertion end 204 of the pin shaft 202 and a distal insertion portion end 234 opposite the proximal insertion portion end 232. The extension portion 240 includes a proximal extension portion end 242 and a distal extension portion end 244 opposite the proximal extension portion end 242 which coincides with the distal end of the pin shaft 202.

Figure 6:
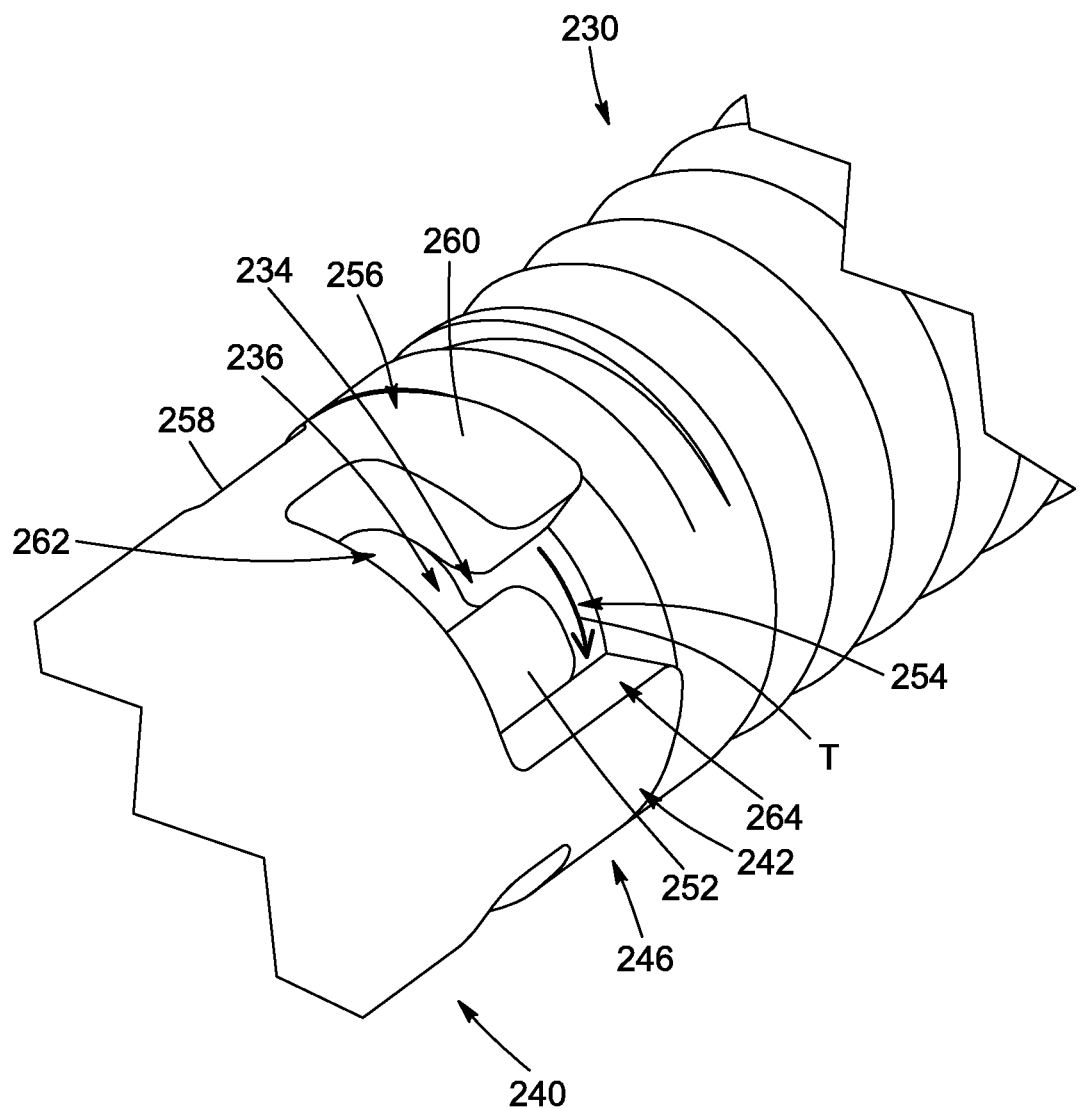
FIG. 6 is an enlarged view of the positioning pin illustrated in FIG. 5.
Figure 7:
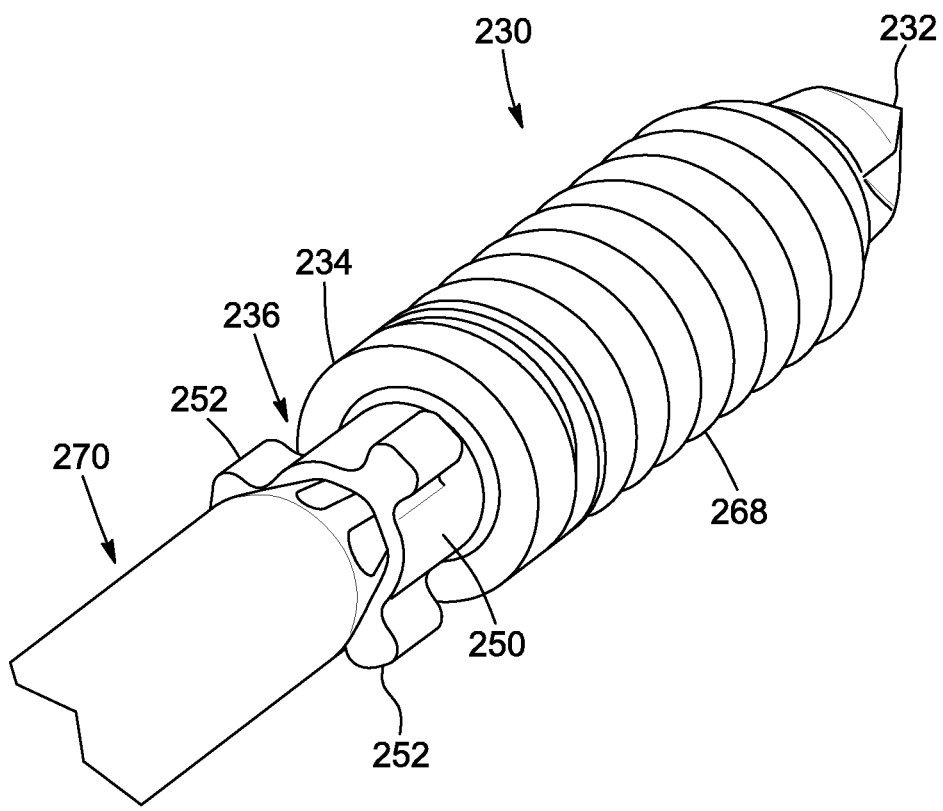
FIG. 7 is another enlarged view of the positioning pin illustrated in FIG. 5, with the extension portion of a pin shaft removed to show a screwing tool engaging an insertion portion.

Referring now to FIGS. 6 and 7, there is shown that the distal insertion portion end 234 of the insertion portion 230 is configured for connection with the proximal extension portion end 242 of the extension portion 240. Specifically, the insertion portion 230 includes a proximal connector 236 located at the distal insertion portion end 234 and the extension portion 240 includes a proximal connector 246 located at the proximal extension portion end 242. The proximal and distal connectors 236, 246 are configured to operatively engage each other to detachably connect the insertion portion 230 to the extension portion 240 to thereby form the entire pin shaft 202.

Figure 8:
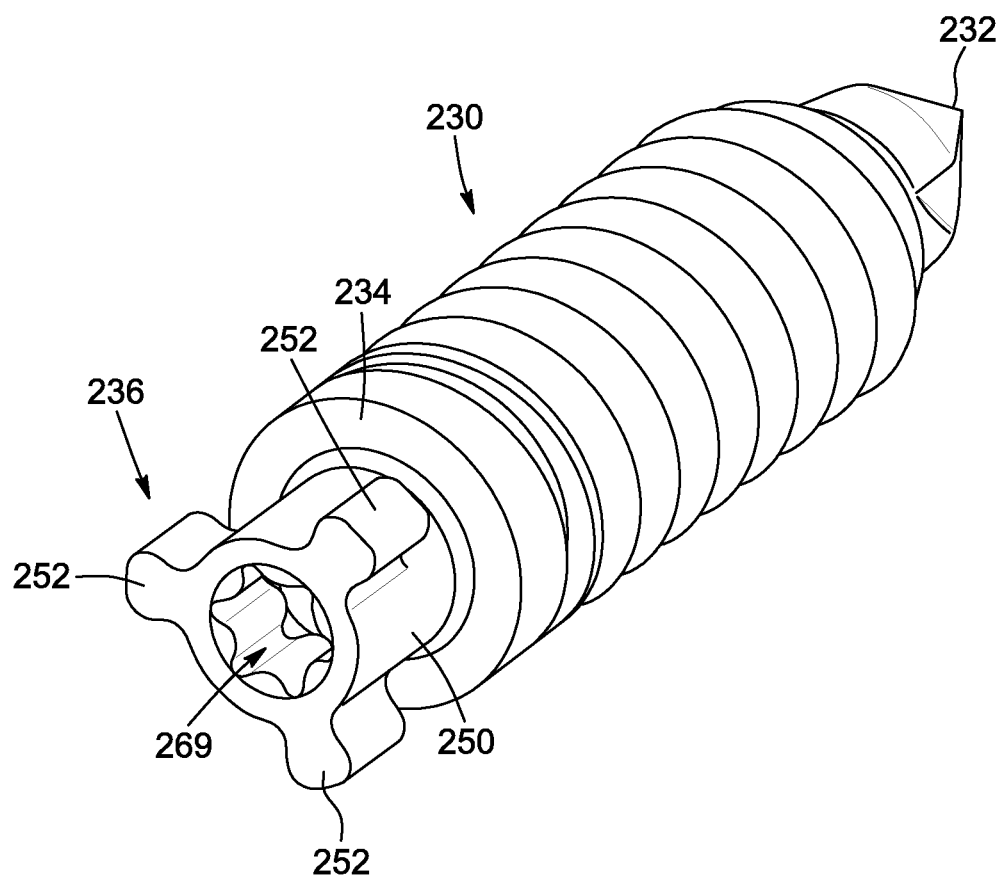
FIG. 8 is a perspective view of the insertion portion for the positioning pin illustrated in FIG. 5.

Referring specifically to FIGS. 6 to 8, the proximal connector 236 includes a central hub 250 extending axially away from the distal insertion portion end 234 and a plurality of radial projections 252 which extends radially away from the central hub 250. The distal connector 246 includes a central recess 254, best shown in FIG. 17, which is sized and shaped for receiving the central hub 250, and a plurality of hook members 256, also best shown in FIG. 17, which are located around the central recess 254. Each hook member 256 is adapted to engage and capture a corresponding radial projection 252 of the proximal connector 236 to thereby lock the extension portion 240 to the insertion portion 230.

Specifically, each hook member 256 is generally L-shaped and includes a base portion 258 which extends away from the proximal extension portion end 242 of the extension portion 240 axially relative to the extension portion 240 (i.e. parallel to a central pin axis P of the positioning pin 200) and an end portion 260 which extends from the base portion 258 in a substantially tangential direction relative to the extension portion 240. In this configuration, each hook member 256 includes a nook 262 defined generally between the end portion 260, the base portion 258 and the proximal extension portion end 242.

As shown in FIG. 6, each radial projection 252 is sized and shaped to be received in the nook 262 of a corresponding hook member 256. Specifically, each radial projection 252 is sized and shaped such that when the radial projection 252 is received in the nook 262, the extension portion 240 is prevented from moving axially relative to the insertion portion 230.

As further shown in FIG. 6, all of the end portions 260 extend from the base portions 258 in a common tangential direction T and are spaced from an adjacent hook member 256 to define an access indent 264 which provides access to the nook 262.

To assemble the extension portion 240 to the insertion portion 230, the central hub 250 of the insertion portion 230 may be inserted in the central recess 254, with the radial projections 252 aligned with and engaging the access indents 264. The extension portion 240 may then be rotated relative to the insertion portion 230 about the central pin axis P in first rotation direction corresponding to the tangential direction T such that the radial projections 252 are received in the nooks 262. To detach the distal connector 246 from the proximal connector 236, the extension portion 240 may be rotated relative to the insertion portion 230 about the central pin axis P in a second rotation direction, opposite the tangential direction T, to move the radial projections 252 out of the nooks 262. The extension portion 240 and the insertion portion 230 may then be moved axially away from each other to thereby disconnect the extension portion 240 from the insertion portion 230.

In the illustrated embodiment, the plurality of hook members 256 includes one hook member 256 for each radial projection 252 such that each radial projection 252 may be captured by a corresponding hook member 256. Specifically, the proximal connector 236 includes three radial projections 252 and the distal connector 246 includes three hook members 256. Alternatively, the proximal and distal connectors 236, 246 may include more or less than three radial projections 252 and three hook members 256. In yet another embodiment, the number of hook members 256 in the distal connector 246 may be different from the number of radial projections 252 in the proximal connector 236.

It will be understood that the proximal and distal connectors 236, 246 may be configured differently. For example, the proximal connector 236 could instead include the central recess 254 and the hook members 256 as described above, while the distal connector 246 includes the central hub 250 and the radial projections 252 as described above. In another embodiment, the proximal and distal connectors 236, 246 may have configurations that are different from the configurations described above. It will be appreciated the other types of proximal and distal connectors 236, 246 can be provided. For instance, the proximal and distal connectors 236, 246 can be screwably connectable together.

In one embodiment, the proximal connector 236 may further be configured so as to be further connectable to at least a portion of an implant to at least assist in securing the implant to the bone 10, as will be explained further below.

In the illustrated embodiment, the positioning pin 200 is configured to be inserted in the bone 10 by being screwed into the bone 10. More specifically, the bone-insertion end 204 of the pin shaft 202 is pointed and the insertion portion 230 of the pin shaft 202 includes a threaded outer surface 268 which extends from the bone-insertion end 204 to at least partway towards the distal insertion portion end 234.

Still in the illustrated embodiment, the positioning pin 200 further includes a tool engagement cavity 269, best shown in FIG. 8, shaped and sized to engage a screwing tool 270, shown in FIGS. 5 and 7, such that rotation of the screwing tool 270 screws the positioning pin 200 into the bone 10. Specifically, the tool engagement cavity 269 is located at the distal insertion portion end 234 of the insertion portion 230 and the extension portion 240 is hollow to provide access to the tool engagement cavity 269 through the extension portion 240. In this embodiment, the screwing tool 270 is elongated such that the screwing tool 270 can extend through the extension portion 240 to reach the tool engagement cavity 269. In the illustrated embodiment, the tool engagement cavity 269 is generally star-shaped to receive a similarly star-shaped end of the screwing tool 270. Alternatively, the tool engagement cavity 269 and the screwing tool 270 could have any other appropriate corresponding shapes. In yet another embodiment, instead of a tool engagement cavity, the positioning pin 200 could instead include a tool engagement protrusion or any other feature which would allow a screwing tool to engage the positioning pin 200 such that rotation of the screwing tool rotates the positioning pin 200.

In one embodiment, the threaded outer surface 268 may be configured such that the positioning pin 200 is screwed into the bone 10 when the screwing tool 270 is rotated about its central pin axis P about a first rotation direction which is opposite the tangential direction T of the hook members 256. In this embodiment, the radial projections 252 of the proximal connector 236 are therefore maintained in their corresponding nooks 262 as the positioning pin 200 is screwed into the bone 10. This configuration ensures that the extension portion 240 does not move axially relative to the insertion portion 230 as the positioning pin 200 is screwed into the bone 10 such that the insertion portion 230 and the extension portion 240 remain connected to each other. This configuration also causes the extension portion 240 to rotate along with the insertion portion 230 as the screwing tool 270 is rotated.

It will be appreciated that by providing the tool engagement cavity 269 on the insertion portion 230, this configuration allows the screwing tool 270 to engage the positioning pin 200 closer to the bone 10 than if the tool engagement cavity 269 was located at the distal end 206 of the pin shaft 202. This may reduce the angular deflection of the positioning pin 200 that may be caused by the torque applied by the screwing tool 270, as well as reduce possible misalignment of the positioning pin 200 while the positioning pin 200 is being screwed into the bone 10. This configuration also allows the torque to be applied directly to the insertion portion 230 instead of exerting strain on the radial projections 252 as the rotation of the extension portion 240 is transmitted to the insertion portion 230.

Alternatively, the tool engagement cavity 269 could be located on the extension portion 240, and more specifically at the distal extension portion end 244, instead of on the insertion portion 230. In this embodiment, the proximal and distal connectors 236, 246 could be configured such that the rotation of the extension portion 240 is transmitted to the insertion portion 230 via the distal connector 246 engaging the proximal connector 236.

Turning now to FIGS. 14 to 16, the milling tool 300 is generally elongated and includes an operative portion 302 which is configured for engaging the bone 10 and a shank portion 304 which is configured to be engaged with and operatively coupled to a rotary actuator, not shown, for rotating the milling tool 300. Specifically, the milling tool 300 is rotatable about the milling axis M to mill the bone 10 when the operative portion 302 engages the bone 10.

In the illustrated embodiment, the operative portion 302 includes a cylindrical body 306 having a milling face 308 configured to contact the bone 10. The milling face 308 may include teeth, protrusion or be substantially abrasive to mill the bone 10 when the milling tool 300 is rotated. In the illustrated embodiment, the milling face 308 is substantially planar so as to create a planar surface on the bone 10 as it mills the bone 10. Specifically, the milling face 308 extends in a milling plane oriented generally orthogonally to the milling axis M. Alternatively, the milling surface 308 could instead extend in a milling plane angled at a different angle relative to the milling axis M. In yet another embodiment, instead of being planar, the milling surface 308 could be curved or have any other shape which would be considered appropriate considering the shape of the implant to be installed and/or the surgery to be performed.

The operative portion 302 further includes a central pin receiving bore 310 which extends through the cylindrical body 306. Specifically, the central pin receiving bore 310 extends along the milling axis M, between the milling face 308 and an inner end face 312 located away from the milling face 308 and towards the shank portion 304. The inner end face 312 defines an abutment portion of the milling tool 300 which may be abutted by the positioning pin 200 when the positioning pin 200 is received in the central pin receiving bore 310 to thereby limit insertion of the positioning pin 200 in the central pin receiving bore 310. Alternatively, instead of including an inner end face 312, the milling tool 300 could include a protrusion or any other feature which could extend into the central pin receiving bore 310 to form an abutment portion for abutting the positioning pin 200.

In the illustrated embodiment, the operative portion 302 further includes a pair of side openings 314 located radially opposite each other and adjacent the inner end face 312. The side openings 314 may allow material such as milled bone fragments or the like to exit the central guiding channel 310 instead of accumulating against the inner end face 312, and may also allow the user to visually confirm that the positioning pin 200 abuts the inner end face 312. Alternatively, the operative portion 302 may not include side openings 314.

In the illustrated embodiment, the shank portion 304 extends substantially along the milling axis M, away from the operative portion 302. Still in the illustrated embodiment, the shank portion 304 is sized and shaped to engage a conventional rotary actuator such as a surgical or orthopaedic drill or the like. The drill could be provided separately from the bone milling kit or, alternatively, the drill may form part of the bone milling kit. In this configuration, the milling tool 300 therefore defines a bit of the drill, and can be removed from the drill such that the drill can therefore be used for other operations besides the milling of the bone 10 using the milling tool 300.

In another embodiment, instead of being distinct from the rotary actuator, the milling tool 300 could instead be integrally formed with the rotary actuator such that the milling tool 300 is not detachable from the rotary actuator.

With references to FIGS. 1 to 20, a method for milling the bone 10 will now be described, in accordance with one embodiment.

As shown in FIGS. 1 and 2, the bone milling guide 100 is first positioned on the bone 10. Specifically, the bone-contacting face 104 of the bone milling guide 100 is placed against the bone 10 and the bone milling guide 100 is positioned at its predetermined location which is defined by the contour of the bone-contacting face 104 which matches the contours of the bone 10 at a specific location on the bone 10.

Figure 4:
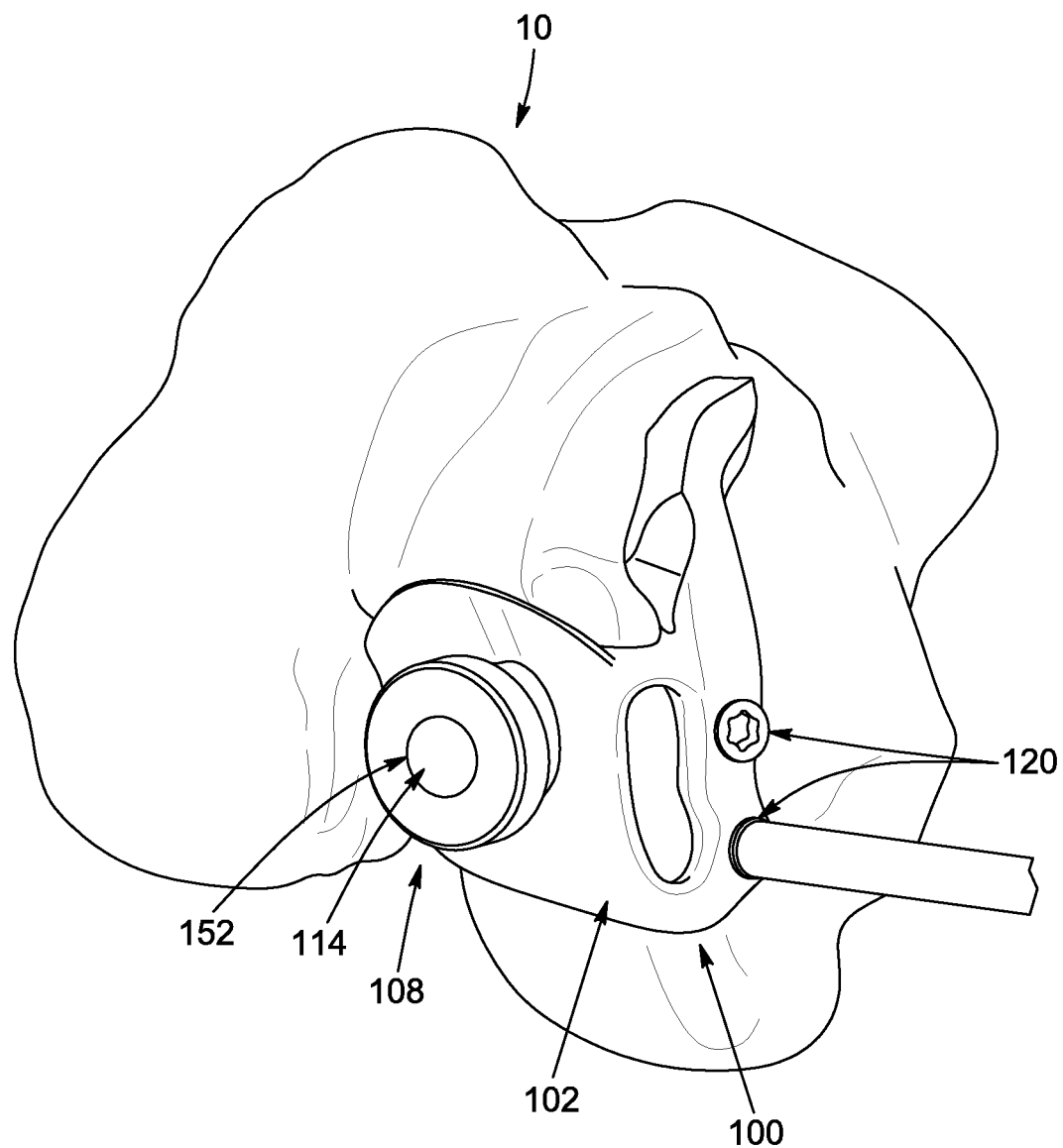
FIG. 4 is another front perspective view of the bone milling guide illustrated in FIG. 1, showing the bone milling guide being fastened to the bone and, more particularly, superposed against a distal end of a femoral condyle.

As shown in FIG. 4, the bone milling guide 100 is then removably attached to the bone 10 using the mechanical fasteners 120 inserted into the corresponding fastener openings 118. Alternatively, instead of using fasteners, the bone milling guide 100 could be secured to the bone 10 using an adhesive material or using any other suitable fastening technique.

As shown in FIGS. 5 and 10, the positioning pin 200 is then aligned with the guiding channel 114 of the bone milling guide 100 and the positioning pin 200 is screwed into the bone 10 using the screwing tool until the stopper 208 abuts the distal end 112 of the guide's positioning pin receiver 108.

As shown in FIG. 11, the stopper 208 is then removed from the pin shaft 202 and, as shown in FIG. 12, the bone milling guide 100 is unfastened from the bone 10. Alternatively, the bone milling guide 100 could instead be unfastened from the bone 10 before the stopper 208 is removed from the pin shaft 202. After the bone milling guide 100 has been removed, only the pin shaft 202 of the positioning pin 200 remains engaged into the bone 10.

As shown in FIG. 13, the bone milling guide 100 is then removed from the bone 10. Specifically, the bone milling guide 100 may be moved away from the bone 10 such that the bone milling guide 100 slides over the positioning pin 200. The bone milling guide 100 is thereby slid towards the distal end 206 of the positioning pin 200 until the bone milling guide 100 is free of the positioning pin 200.

As shown in FIG. 14, the milling tool 300 is then aligned with the positioning pin 200 such that the milling axis M coincides with the pin axis P, and the milling tool 300 is inserted over the pin shaft 202 of the positioning pin 200 such that the pin shaft 202 is received in the central pin receiving bore 310.

As shown in FIGS. 15 and 16, the milling tool 300 is then slidably moved along the pin shaft 202 until the milling face 308 contacts the bone 10. The milling tool 300 is rotated using the rotary actuator while the milling tool 300 is further moved towards the bone 10 to thereby mill the bone 10. The milling tool 300 may be moved towards the bone 10 until the distal end 206 of the pin shaft 202 abuts the inner end face 312 of the milling tool 300, as shown in FIG. 16, which prevents the milling tool 300 from being further moved towards the bone 10.

The milling of the bone 10 therefore creates a recess in the bone 10. It will be appreciated that the depth of this recess depends on the distance between the second end 206 of the pin shaft 202 and the bone 10, i.e. the length by which the pin shaft 202 extends out of the bone 10. As explained above, the length by which the pin shaft 202 extends out of the bone 10 is defined by the location of the stopper 208 on the pin shaft 202 and the distance between the distal end 112 of the guide's positioning pin receiver 108 and bone-contacting face 104. Specifically, once the positioning pin 20 is inserted in the bone 10 as described above, the distance between the distal end 206 of the pin shaft 202 and the bone 10 is roughly equal to the sum of a distance between the distal end 206 of the pin shaft 202 and the stopper 208 and a distance between the distal end 112 of the positioning pin receiver 108 and the bone-contacting face 104 of the bone milling guide 100.

Figure 17:
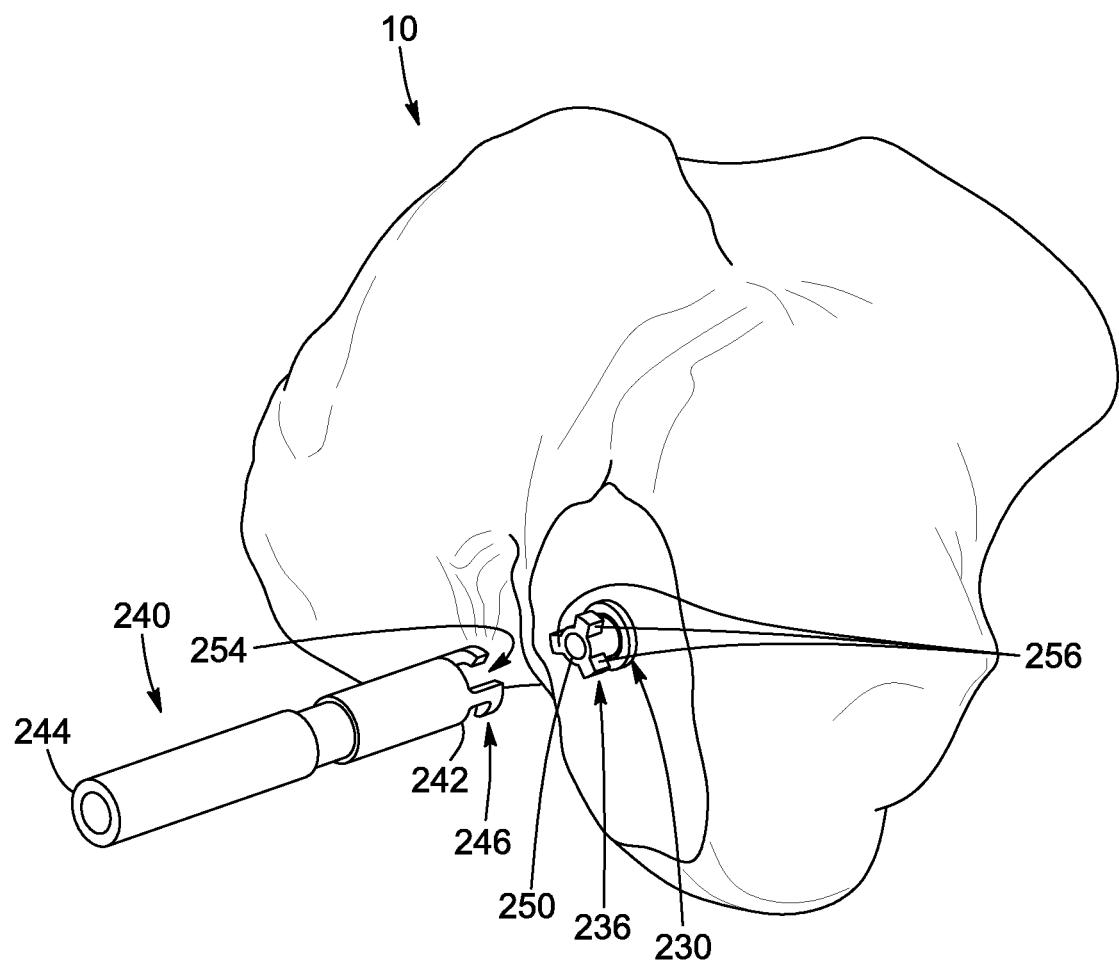
FIG. 17 is a partially exploded perspective view of the positioning pin illustrated in FIG. 5, showing the insertion portion of the positioning pin inserted in the bone and the extension portion detached from the insertion portion.

As shown in FIG. 17, once the bone 10 is milled, the milling tool 300 is removed by sliding the milling tool 300 away from the bone 10 until the milling tool 300 is free from the positioning pin 200. As further shown in FIG. 17, the extension portion 240 of the pin shaft 202 is removed from the insertion portion 230 as described above. In the illustrated embodiment, when the extension portion 240 is removed, at least a portion of the insertion portion 230 extends out of the bone 10. Specifically, the proximal connector 236 extends out of the bone 10 and is therefore accessible to the user. In one embodiment, the proximal connector 236 is further used to attach the implant to the bone 10. Alternatively, the proximal connector 236 may simply be used to locate the implant on the bone 10 to a desired location. In yet another embodiment, the insertion portion 230 of the pin shaft 202 may not be used for mounting the implant to the bone 10 and the insertion portion 230 may be removed from the bone 10 before mounting the implant on the bone 10.

Figure 18:
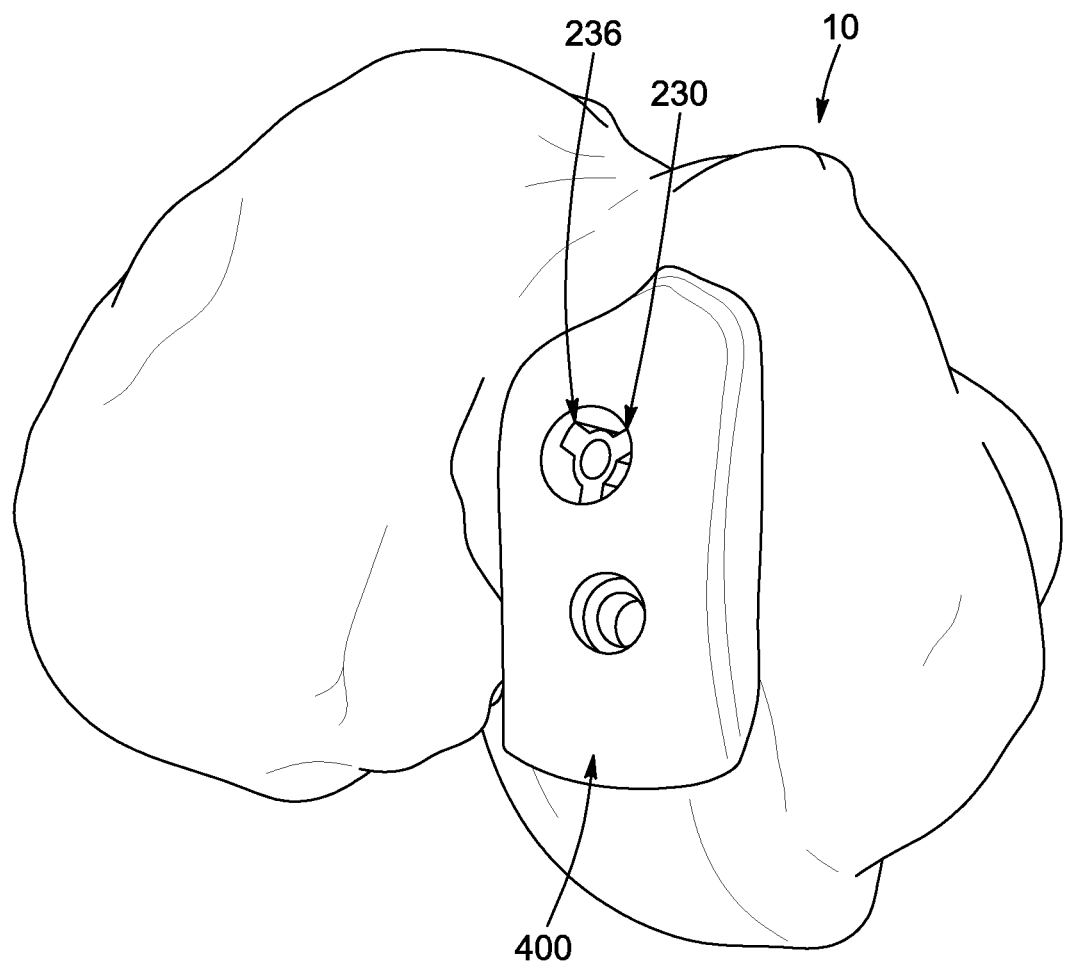
FIG. 18 is a front perspective view of a first cut validation tool mounted to the insertion portion illustrated in FIG. 17, in accordance with one embodiment.
Figure 19:
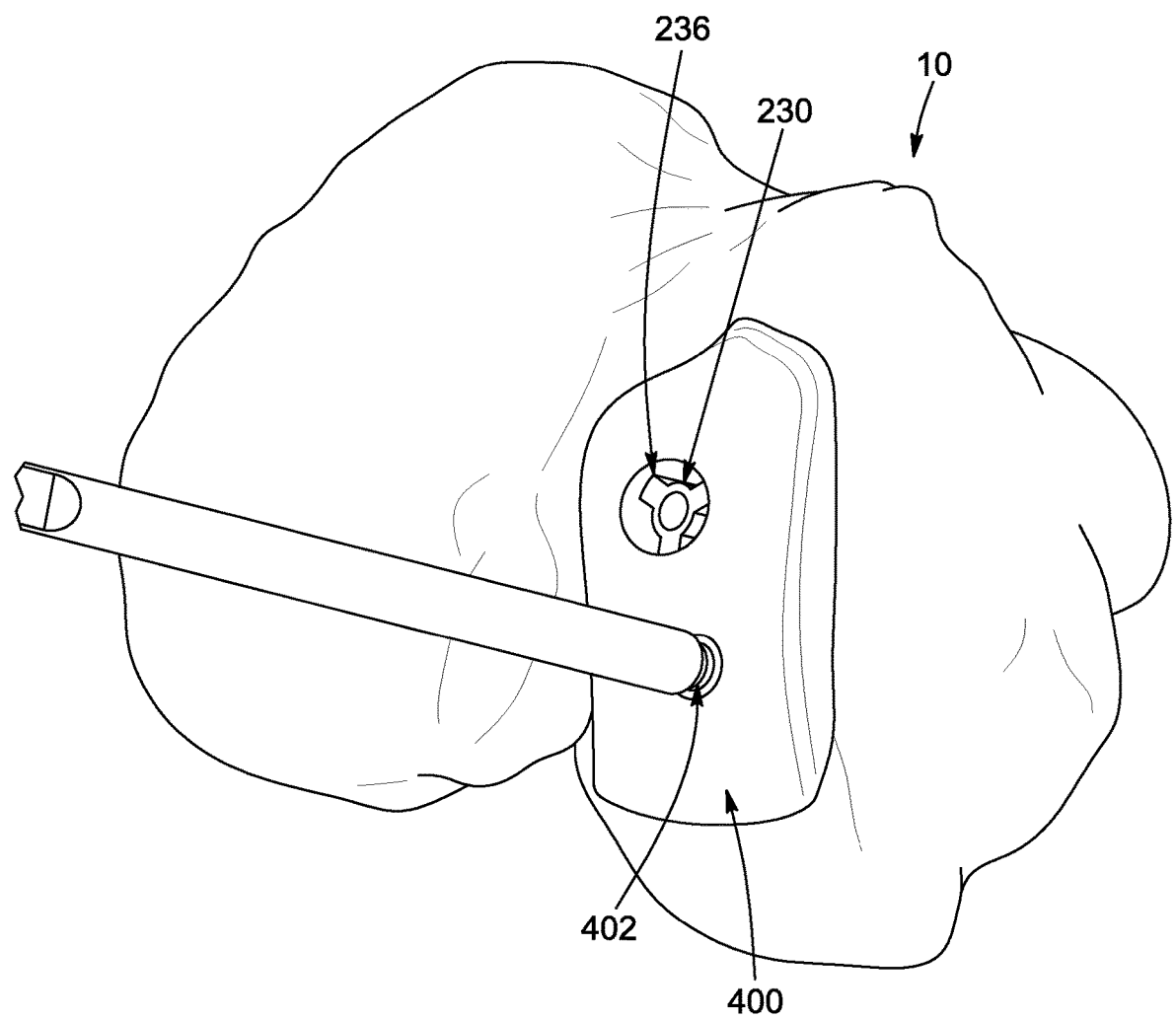
FIG. 19 is a front perspective view of the first cut validation tool illustrated in FIG. 18, showing the first cut validation tool being fastened to the bone and, more particularly, superposed against the distal end of the femoral condyle.
Figure 20:
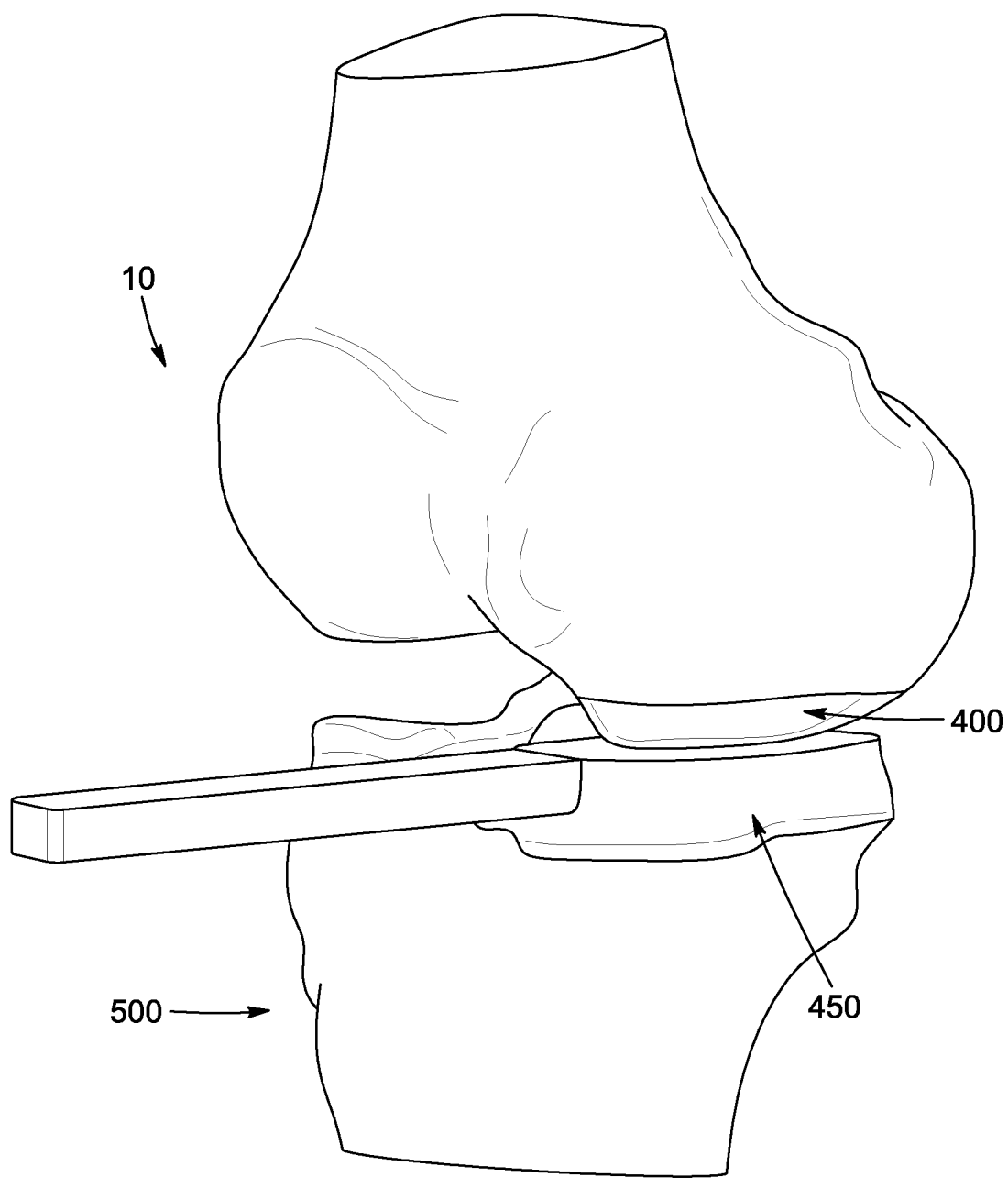
FIG. 20 is a front perspective view of the first cut validation tool illustrated in FIG. 18 mounted to the bone, with a second cut validation tool superposed against a patient's tibia bone opposite the first cut validation tool to test laxity of the patient's knee.

As shown in FIGS. 18 to 20, before installing the implant on the bone 10, the milling of the bone 10 may first be measured or verified. More specifically, a first cut validation tool 400 (such as a femoral cut validation tool in the embodiment shown in FIGS. 18 to 20) may be placed against the bone 10 in the recess formed in the bone 10. The first cut validation tool 400 may be configured to engage the insertion portion 230 inserted in the bone 10 to properly position the first cut validation tool 400. As shown in FIG. 19, the first cut validation tool 400 may further be fastened to the bone 10 using a fastener 402. Alternatively, the first cut validation tool 400 may be fastened using more than one fastener or using any other suitable fastening technique. For example, the first cut validation tool 400 could be fastened to and held in place by the insertion portion 230 inserted in the bone 10, or could In the illustrated embodiment, a recess, or cut or resection, has also been created in the patient's tibia 500 opposite the medial condyle of the patient's femur. A second cut validation tool 450 (such as a tibial cut validation tool in the embodiment shown in FIGS. 18 to 20), sized and shaped to engage the recess, or resected section, of the tibia 500, is positioned in the recess of the tibia 500. The patient's femur and tibia may then be moved relative to each other to test the laxity of the knee in extension.

Figure 21:
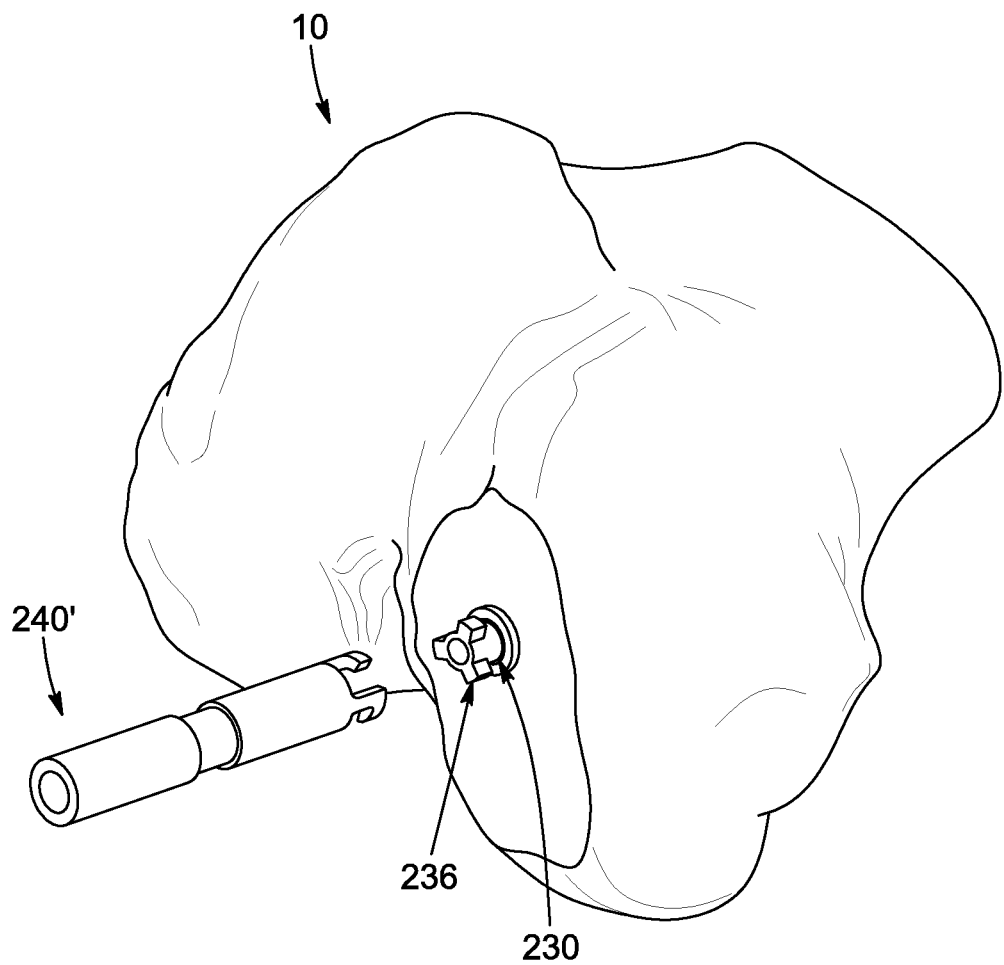
FIG. 21 is a partially exploded perspective view of the positioning pin illustrated in FIG. 5, showing the insertion portion of the positioning pin inserted in the bone with the extension portion detached from the insertion portion and with a second distal extension portion located proximal the insertion portion of the positioning pin for attachment thereto.

If the knee is tight in extension, it may be desirable to further ream the medial condyle to increase the depth of the recess in the medial condyle. Specifically, the first and second cut validation tools 400, 450 may be removed, and a second extension portion 240', shown in FIG. 21, may be connected to the insertion portion 230 of the positioning pin 200. This second distal extension portion 240' is substantially similar to the extension portion 240, but is substantially shorter than the extension portion 240. It will be appreciated that by inserting the milling tool 300 over the second distal extension portion 240', rotating the milling tool 300 and moving the milling tool 300 towards the bone 10 until the second distal extension portion 240' abuts the inner end face 312 of the milling tool 300, the bone 10 will be further milled. Specifically, the recess depth will be increased by a distance corresponding to a difference between the length of the extension portion 240 and the length of the second distal extension portion 240'. In one embodiment, the second distal extension portion 240' may be removed from the insertion portion 230 and the recess may then be further measured using the first and second cut validation tools 400, 450. If it is desired to again increase the depth of the recess, a third extension portion, not shown, shorter than the second distal extension portion 240' could be connected to the insertion portion 230 and the bone 10 may be further milled, and so on until the laxity of the knee in extension is considered to be satisfactory.

In one embodiment, the bone milling kit could include a plurality of extension portions 240, each extension portion having a length which is different than the length of the other extension portions. Alternatively, the bone milling kit could include a plurality of positioning pins 200, each one having a different distance between the distal end of the positioning pin 200 and the stopper 208. Instead of removing the extension portion 240 to further mill the bone 10, the entire pin shaft 202 could be removed and replaced with another positioning pin 200.

In one embodiment, the first and second cut validation tools 400, 450 may form part of the bone milling kit. Alternatively, the first and second cut validation tools 400, 450 may not form part of the bone milling kit and may instead be provided separately from the bone milling kit.

It will be appreciated that the above embodiments are provided as examples only, and that various other embodiments could be considered. For example, in the above-described embodiments, the positioning pin 200 is self-tapping and does not require a bore to be pre-drilled in the bone 10. Alternatively, a bore could be pre-drilled in the bone 10 for receiving the positioning pin 200.

Figure 22:
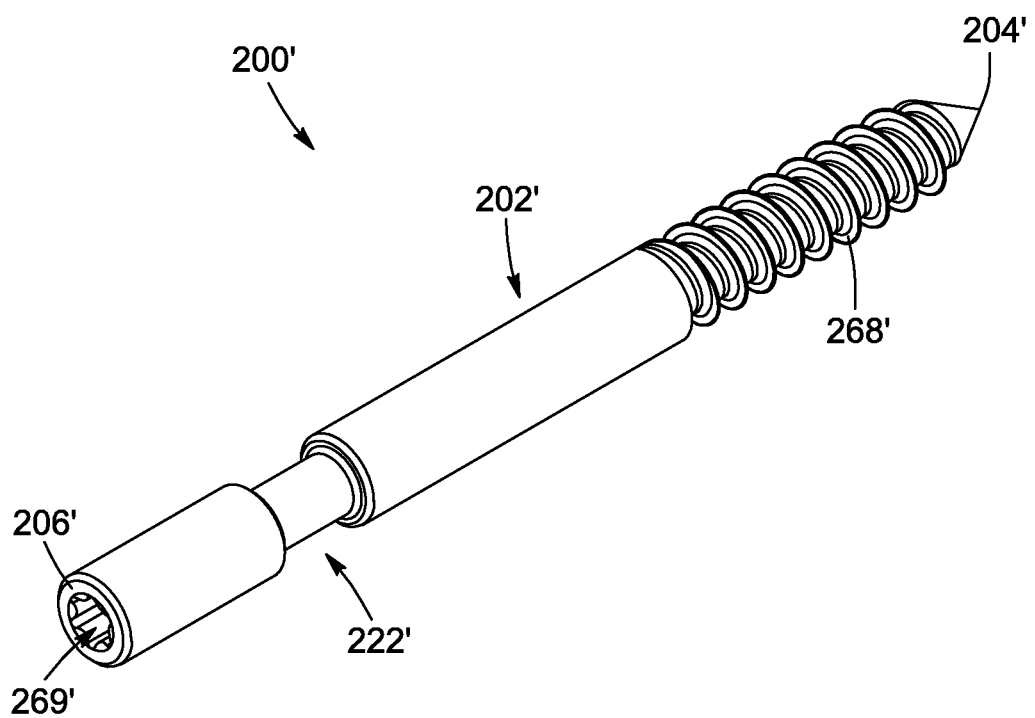
FIG. 22 is a front perspective view of a positioning pin, in accordance with another embodiment.

Referring now to FIG. 22, there is shown a positioning pin 200' adapted to be guided by the bone milling guide 100, in accordance with another embodiment. Similarly to the positioning pin 200, the positioning pin 200' includes a pin shaft 202' having a bone-insertion end 204' and a distal end 206' opposite the bone-insertion end 204'. Further similarly to the pin shaft 202, the bone-insertion end 204' is pointed and the pin shaft 202' includes a threaded outer surface 268' which extends from the bone-insertion end 204' to at least partway towards the distal end 206' of the pin shaft 202'. Still similarly to the pin shaft 202, the pin shaft 202' further includes an annular groove 222' sized and shaped to receive a stopper such as the stopper 208 illustrated in FIG. 9.

In the embodiment illustrated in FIG. 22, instead of including an insertion portion and an extension portion distinct from the insertion portion, the pin shaft 202' is made of a single piece of material. More specifically, the pin shaft 202' extends continuously between the bone-insertion end 204' and the distal end 206'.

Still in the embodiment illustrated in FIG. 22, the positioning pin 200' further includes a tool engagement cavity 269' shaped and sized to engage a screwing tool such as the screwing tool 270 shown in FIG. 7 for screwing the positioning pin 200' into the patient's bone 10. In this embodiment, the tool engagement cavity 269' is defined in the distal end 206' of the pin shaft 202'.

In the embodiment illustrated in FIG. 22, the tool engagement cavity 269' is generally star-shaped to receive a similarly star-shaped end of the screwing tool 270. Alternatively, the tool engagement cavity 269' and the screwing tool 270 could have any other appropriate corresponding shapes. In yet another embodiment, instead of a tool engagement cavity, the positioning pin 200' could instead include a tool engagement protrusion or any other feature which would allow a screwing tool to engage the positioning pin 200' such that rotation of the screwing tool rotates the positioning pin 200'.

In use, the positioning pin 200', with the stopper 208 received in the annular groove 222', may be inserted in the guide's guiding channel 114 with the bone-insertion end 204' disposed towards the patient's bone 10. The screwing tool 270 could then be engaged in the tool engagement cavity 269' and rotated in a first rotation direction, such as a clockwise direction for example, to screw the positioning pin 200' into the bone 10 until the stopper 208 abuts the bone milling guide 100. The bone 10 could then be milled using the milling tool 300 as described above.

In one embodiment, once the bone 10 has been suitably milled, the positioning pin 200' can be altogether removed from the bone 10 by engaging the screwing tool 270 in the tool engagement cavity 269' and rotating it in a second rotation direction opposite the first rotation direction, such as a counterclockwise direction for example, to thereby unscrew the positioning pin 200' from the bone 10.

In one embodiment, the positioning pin 200' can then be replaced by another positioning pin which is substantially similar to the positioning pin 200', but which is shorter in length such that the bone 10 may be further milled using the milling tool 300, as described above.

It will be understood that the configuration described above is merely provided as an example and that various other configurations may be possible. For example, in the embodiments described above, the stopper 208 cooperates with the abutment portion 115 of the bone milling guide 100 to provide an indication that the positioning pin 200 is inserted in the bone 10 at a predetermined depth, which is defined by the location of the stopper 208 along the pin shaft 202. Alternatively, the bone milling kit may not include a stopper 208 abutting a portion of the bone milling guide 100. Instead, the positioning pin 200 may include a pin depth determination element (or pin depth indicator) located at a predetermined indicator position on the pin shaft 202 and the bone milling guide 100 may include a guide depth determination element (or guide depth indicator) configured to cooperate with the pin depth determination element when the positioning pin 200 is inserted into the bone 10 through the guiding channel 114 of the bone milling guide 100 to provide an indication that the positioning pin 200 is inserted in the bone 10 at a predetermined depth. For example, the guide depth determination element may include the distal end 112 of the guide's positioning pin receiver 108 and the pin depth determination element may include an indentation, e.g. an annular groove, defined on the pin shaft 202. During surgery, the positioning pin 200 can therefore be inserted into the bone 10 through the positioning pin receiver 108 until the indentation is aligned with the distal end of the positioning pin receiver 108, thereby providing the user performing the surgery with a visual indication that the positioning pin 200 is inserted in the bone 10 at the predetermined depth.

In yet another embodiment, the positioning pin 200 could include a plurality of indentations, each one corresponding to a unique predetermined depth of the positioning pin 200 in the bone 10. The user performing the surgery could therefore select which indentation to align with the distal end 112 of the positioning pin receiver 108 in accordance with a desired depth of the positioning pin 200 in the bone 10.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative and non-limiting and it will be understood by persons skilled in the art that other variants and modifications may be made without departing from the scope of the invention as defined in the claims appended hereto.

The invention claimed is:

1. A surgical kit for milling a bone, the surgical kit comprising:
   a milling tool rotatable about a milling axis, the milling tool including a milling face for contacting the bone, a central pin receiving bore extending along the milling axis and an abutment portion extending into the central pin receiving bore;
   a positioning pin insertable in the bone and engageable by the milling tool for guiding the milling tool along the milling axis and towards the bone, the positioning pin including a pin shaft receivable in the central pin receiving bore of the milling tool and a pin depth determination element located at a predetermined position on the pin shaft, the pin shaft being abuttable against the abutment portion of the milling tool to prevent further movement of the milling tool towards the bone along the milling axis; and
   a bone milling guide positionable at a predetermined location on the bone and engageable by the positioning pin when the positioning pin is inserted into the bone, the bone milling guide including a pin shaft guiding channel sized and shaped to receive the pin shaft therein, the bone milling guide further including a guide depth determination element located adjacent the pin shaft guiding channel, the guide depth determination element being configured to cooperate with the pin depth determination element to provide an indication that the positioning pin is inserted in the bone at a predetermined depth.

2. The surgical kit as claimed in claim 1, wherein the pin depth determination element comprises a stopper mounted to the pin shaft and wherein the guide depth determination element comprises an abutment portion, the abutment portion being abuttable against the stopper when the positioning pin is inserted into the bone through the pin shaft guiding channel to prevent further insertion of the positioning pin into the bone.

3. The surgical kit as claimed in claim 2, wherein the stopper is removably mounted to the pin shaft.

4. The surgical kit as claimed in claim 2, wherein the stopper extends radially outwardly from the pin shaft.

5. The surgical kit as claimed in claim 4, wherein the stopper is penannular and comprises an inner side face defining a central opening, an outer side face spaced radially outwardly from the inner side face and an access notch extending from the outer side face to the inner side face.

6. The surgical kit as claimed in claim 5, wherein the notch tapers from the outer side face to the inner side face.

7. The surgical kit as claimed in claim 5, wherein the pin shaft comprises an annular groove, the stopper being sized and shaped to be received in the central opening of the stopper to prevent movement of the stopper along the pin shaft.

8. The surgical kit as claimed in claim 1, wherein the pin shaft comprises a proximal pin portion insertable into the bone and a distal pin portion detachably connectable to the proximal pin portion.

9. The surgical kit as claimed in claim 8, wherein the proximal pin portion comprises a proximal connector and the distal pin portion comprises a distal connector engageable with the proximal connector to connect the proximal pin portion to the distal pin portion.

10. The surgical kit as claimed in claim 9, wherein the proximal and distal connectors are configured such that rotation of the distal shaft portion in a first rotation direction rotates the proximal shaft portion in the first rotation along with the distal shaft portion, and rotation of the distal shaft portion in a second rotation direction opposite the first rotation direction detaches the distal shaft portion from the proximal shaft portion.

11. The surgical kit as claimed in claim 10, wherein the distal pin portion is hollow to allow an elongated screwing tool to extend longitudinally through the distal pin portion to engage the distal end of the proximal pin portion such that rotation of the elongated tool in the first rotation direction rotates the positioning pin.

12. The surgical kit as claimed in claim 1, wherein the bone milling guide including a guide body having a bone-contacting face configured to be placed against the bone and a pin-engaging face opposite the bone-contacting face, the bone-contacting face being sized and shaped to substantially conform to surface contours of the bone at the predetermined location on the bone.

13. The surgical kit as claimed in claim 12, wherein the pin shaft guiding channel comprises a positioning pin receiver extending away from the pin-engaging face of the guide body, the positioning pin receiver having a bone-insertion end secured to the guide body and a distal end located away from the body, the distal end comprising the abutment portion of the bone milling guide.

14. The surgical kit as claimed in claim 1, wherein the milling tool comprises an operative portion engageable with the bone to mill the bone and a shank portion operatively couplable with a rotary actuator for rotating the milling tool.

15. The surgical kit as claimed in claim 14, wherein the operative portion of the milling tool comprises a milling face for contacting the bone, the milling face extending in a milling plane oriented generally orthogonally to the milling axis.

16. The surgical kit as claimed in claim 15, wherein the central pin receiving bore extends along the milling axis between the milling face and an inner end face located away from the milling face and towards the shank portion, the inner end face defining the abutment portion of the milling tool.

17. The surgical kit as claimed in claim 16, wherein the operative portion further comprises a pair of side openings located radially opposite each other and adjacent the inner end face.

* * * * *